(12) United States Patent
Freytag

(10) Patent No.: US 10,275,797 B2
(45) Date of Patent: Apr. 30, 2019

(54) SYSTEMS AND METHODS FOR AUTOMATICALLY DISENGAGING A BRAKING FUNCTION OF A VEHICLE

(71) Applicant: NIO USA, Inc., San Jose, CA (US)

(72) Inventor: Patrick Freytag, Santa Clara, CA (US)

(73) Assignee: NIO USA, Inc., San Jose, CA (US)

( * ) Notice: Subject to any disclaimer, the term of this patent is extended or adjusted under 35 U.S.C. 154(b) by 15 days.

(21) Appl. No.: 15/396,581

(22) Filed: Dec. 31, 2016

(65) Prior Publication Data

US 2018/0141545 A1 May 24, 2018

Related U.S. Application Data

(60) Provisional application No. 62/424,976, filed on Nov. 21, 2016.

(51) Int. Cl.
*B60W 10/18* (2012.01)
*B60W 10/20* (2006.01)
(Continued)

(52) U.S. Cl.
CPC ............ *G06Q 30/0266* (2013.01); *A61B 5/01* (2013.01); *A61B 5/024* (2013.01); *A61B 5/08* (2013.01); *A61B 5/165* (2013.01); *A61B 5/18* (2013.01); *B60R 11/04* (2013.01); *B60S 1/62* (2013.01); *B60W 10/04* (2013.01); *B60W 10/18* (2013.01); *B60W 10/20* (2013.01); *B60W 30/09* (2013.01); *B60W 40/04* (2013.01); *B60W 40/08* (2013.01); *B60W 40/09* (2013.01); *B60W 40/105* (2013.01); *B60W 50/0097* (2013.01); *B60W 50/0098* (2013.01); *B60W 50/08* (2013.01); *B60W 50/082* (2013.01); *B62D 15/00* (2013.01); *G01C 21/3682* (2013.01); *G01C 21/3691* (2013.01); *G01C 21/3697* (2013.01); *G01S 13/862* (2013.01); *G01S 13/865* (2013.01); *G01S 13/867* (2013.01);
(Continued)

(58) Field of Classification Search
CPC ....... B60W 10/18; B60W 10/20; B60W 30/09
See application file for complete search history.

(56) References Cited

U.S. PATENT DOCUMENTS

| 2010/0010723 A1* | 1/2010 | Taki | ............. B60W 30/08 701/102 |
| 2013/0054103 A1* | 2/2013 | Herink | ............. B60T 7/22 701/65 |

(Continued)

OTHER PUBLICATIONS

Davies, "This NIO EP9 performance EV wants to be the Tesla of Supercars," SlashGear, 2016, retrieved from https//www.slashgear.com/nextev-nio-ep9-car-tesla-of-performance-evs-21464829, 9 pages.
(Continued)

*Primary Examiner* — Anshul Sood
(74) *Attorney, Agent, or Firm* — Sheridan Ross P.C.

(57) ABSTRACT

Embodiments herein relate to an autonomous vehicle or self-driving vehicle with a vehicle control system. The vehicle control system can determine, prior to and/or during a collision, whether an escape path exits. If an escape path exists, the brakes are disengaged such that at least some of the energy and/or momentum from a colliding vehicle is transferred and a jolt or shock experienced by an occupant is reduced.

20 Claims, 18 Drawing Sheets

(51) Int. Cl.
- B60W 30/09 (2012.01)
- G06Q 30/02 (2012.01)
- G01C 21/36 (2006.01)
- G06F 17/30 (2006.01)
- B60R 11/04 (2006.01)
- B60S 1/62 (2006.01)
- G01S 13/86 (2006.01)
- G02B 27/00 (2006.01)
- B60W 50/00 (2006.01)
- G05D 1/00 (2006.01)
- G05D 1/02 (2006.01)
- A61B 5/01 (2006.01)
- A61B 5/024 (2006.01)
- A61B 5/08 (2006.01)
- A61B 5/16 (2006.01)
- A61B 5/18 (2006.01)
- B60W 40/09 (2012.01)
- B60W 50/08 (2012.01)
- G08G 1/16 (2006.01)
- B60W 10/04 (2006.01)
- B60W 40/04 (2006.01)
- B60W 40/08 (2012.01)
- B60W 40/105 (2012.01)
- G01S 15/02 (2006.01)
- B62D 15/00 (2006.01)
- G01S 7/40 (2006.01)
- G01S 7/497 (2006.01)
- G01S 13/93 (2006.01)

(52) U.S. Cl.
CPC .......... *G01S 15/02* (2013.01); *G02B 27/0006* (2013.01); *G05D 1/0061* (2013.01); *G05D 1/0088* (2013.01); *G05D 1/0212* (2013.01); *G05D 1/0214* (2013.01); *G05D 1/0221* (2013.01); *G05D 1/0276* (2013.01); *G06F 17/30241* (2013.01); *G06F 17/30861* (2013.01); *G06Q 30/0269* (2013.01); *G08G 1/161* (2013.01); *G08G 1/163* (2013.01); *G08G 1/164* (2013.01); *G08G 1/165* (2013.01); *G08G 1/166* (2013.01); *B60W 2040/0809* (2013.01); *B60W 2050/0004* (2013.01); *B60W 2050/0014* (2013.01); *B60W 2300/34* (2013.01); *B60W 2510/08* (2013.01); *B60W 2510/18* (2013.01); *B60W 2520/04* (2013.01); *B60W 2520/105* (2013.01); *B60W 2540/18* (2013.01); *B60W 2540/22* (2013.01); *B60W 2540/28* (2013.01); *B60W 2540/30* (2013.01); *B60W 2550/10* (2013.01); *B60W 2550/30* (2013.01); *B60W 2710/18* (2013.01); *B60W 2710/20* (2013.01); *B60W 2750/40* (2013.01); *B60W 2900/00* (2013.01); *G01S 2007/4043* (2013.01); *G01S 2007/4977* (2013.01); *G01S 2013/935* (2013.01); *G01S 2013/936* (2013.01); *G01S 2013/9325* (2013.01); *G01S 2013/9342* (2013.01); *G01S 2013/9346* (2013.01); *G01S 2013/9353* (2013.01); *G01S 2013/9357* (2013.01); *G01S 2013/9375* (2013.01); *G01S 2013/9378* (2013.01); *G01S 2013/9382* (2013.01); *G01S 2013/9385* (2013.01); *G01S 2013/9389* (2013.01); *G05D 2201/0212* (2013.01)

(56) References Cited

U.S. PATENT DOCUMENTS

2016/0347310 A1* 12/2016 Moran .................. B60W 30/09
2017/0120804 A1* 5/2017 Kentley ............... G05D 1/0088

OTHER PUBLICATIONS

Kautonen, "NextEV unveils the NIO EP9 electric supercar in London," Autoblog, 2016, retrieved from http://www.autoblog.com/2016/11/21/nextev-unveiles-the-nio-ep9-electric-supercar-in-london/, 3 pages.

White, "NextEV's NIO IP9 is an incredible four-wheel-drive electric hypercar," WIRED, 2016, retrieved from http://www.wired.co.uk/article/nextev-hypercar-nio-ep9, 6 pages.

* cited by examiner

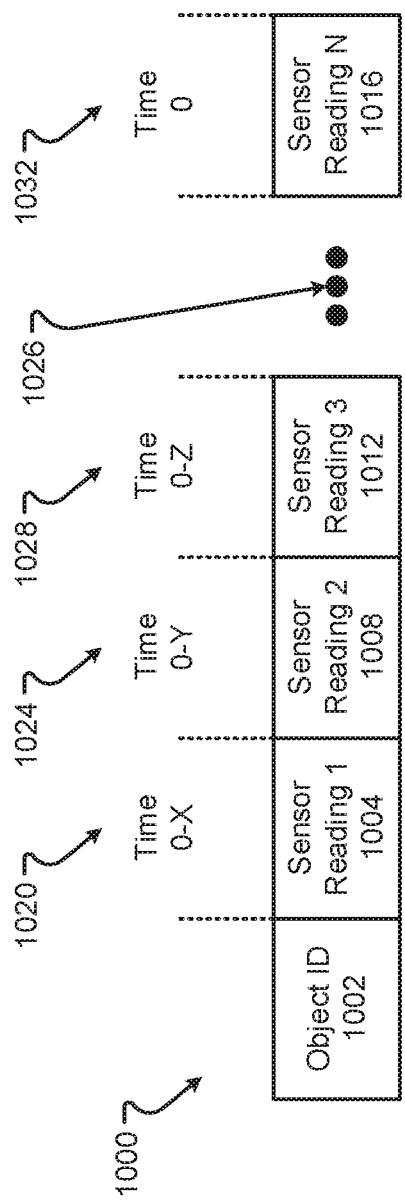
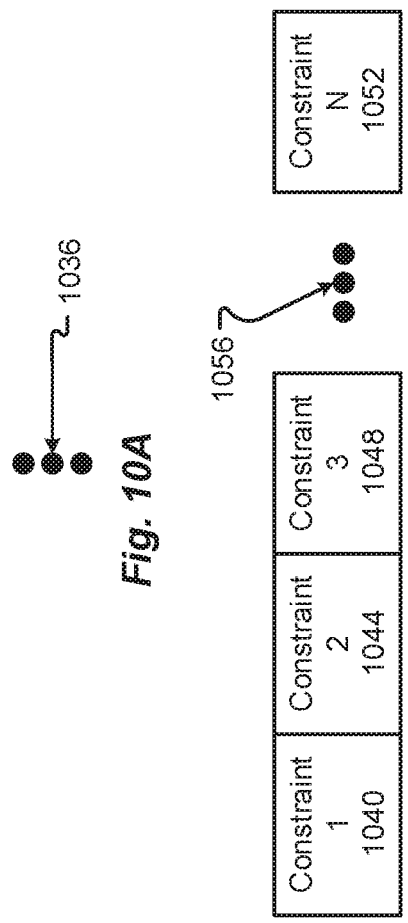
Fig. 10A
Fig. 10B

SYSTEMS AND METHODS FOR AUTOMATICALLY DISENGAGING A BRAKING FUNCTION OF A VEHICLE

CROSS REFERENCE TO RELATED APPLICATIONS

The present application claims the benefits of and priority, under 35 U.S.C. § 119(e), to U.S. Provisional Application Ser. No. 62/424,976, filed on Nov. 21, 2016, entitled "Next Generation Vehicle." The entire disclosure of the application listed above is hereby incorporated by reference, in its entirety, for all that it teaches and for all purposes.

FIELD

The present disclosure is generally directed to vehicle systems, in particular, toward electric and/or hybrid-electric vehicles.

BACKGROUND

In recent years, transportation methods have changed substantially. This change is due in part to a concern over the limited availability of natural resources, a proliferation in personal technology, and a societal shift to adopt more environmentally friendly transportation solutions. These considerations have encouraged the development of a number of new flexible-fuel vehicles, hybrid-electric vehicles, and electric vehicles.

While these vehicles appear to be new, they are generally implemented via a number of traditional subsystems that are merely tied to an alternative power source. In fact, the design and construction of the vehicles is limited to standard frame sizes, shapes, materials, and transportation concepts. Among other things, these limitations fail to take advantage of the benefits of new technology, power sources, and support infrastructure.

BRIEF DESCRIPTION OF THE DRAWINGS

FIGS. 10A-C illustrate data structures in accordance with embodiments of the present disclosure;

DETAILED DESCRIPTION

Embodiments of the present disclosure will be described in connection with a vehicle and, in some embodiments, an electric vehicle, rechargeable electric vehicle, and/or hybrid-electric vehicle and associated systems.

Figure 1:
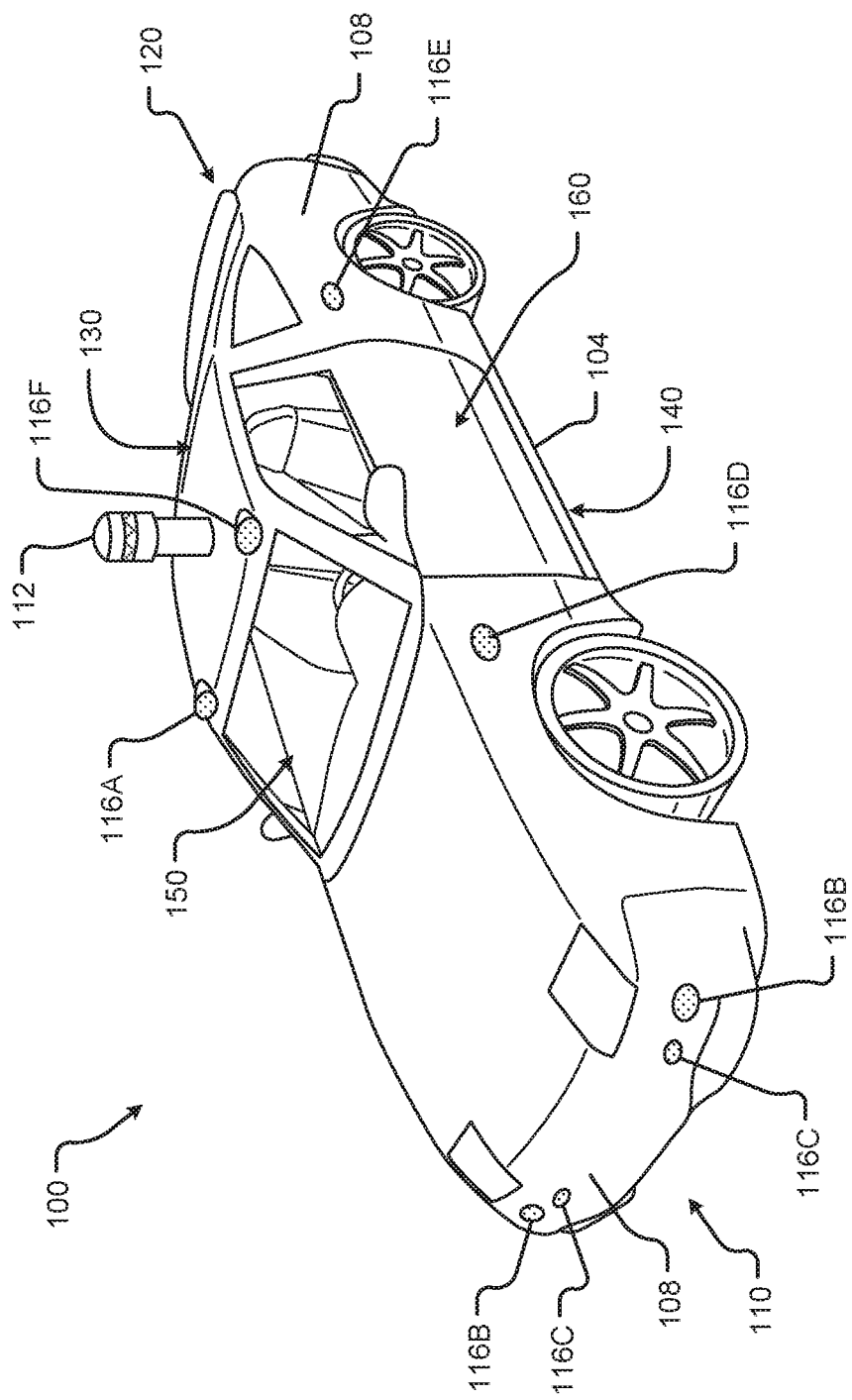
FIG. 1 shows a vehicle in accordance with embodiments of the present disclosure.

FIG. 1 shows a perspective view of a vehicle 100 in accordance with embodiments of the present disclosure. The vehicle 100 comprises a vehicle front 110, vehicle aft or rear 120, vehicle roof 130, at least one vehicle side 160, a vehicle undercarriage 140, and a vehicle interior 150. In any event, the vehicle 100 may include a frame 104 and one or more body panels 108 mounted or affixed thereto. The vehicle 100 may include one or more interior components (e.g., components inside an interior space 150, or user space, of a vehicle 100, etc.), exterior components (e.g., components outside of the interior space 150, or user space, of a vehicle 100, etc.), drive systems, controls systems, structural components, etc.

Although shown in the form of a car, it should be appreciated that the vehicle 100 described herein may include any conveyance or model of a conveyance, where the conveyance was designed for the purpose of moving one or more tangible objects, such as people, animals, cargo, and the like. The term "vehicle" does not require that a conveyance moves or is capable of movement. Typical vehicles may include, but are in no way limited to, cars, trucks, motorcycles, busses, automobiles, trains, railed conveyances, boats, ships, marine conveyances, submarine conveyances, airplanes, space craft, flying machines, human-powered conveyances, and the like.

In some embodiments, the vehicle 100 may include a number of sensors, devices, and/or systems that are capable of assisting in driving operations. Examples of the various sensors and systems may include, but are in no way limited to, one or more of cameras (e.g., independent, stereo, combined image, etc.), infrared (IR) sensors, radio frequency (RF) sensors, ultrasonic sensors (e.g., transducers, transceivers, etc.), RADAR sensors (e.g., object-detection sensors and/or systems), LIDAR systems, odometry sensors and/or devices (e.g., encoders, etc.), orientation sensors (e.g., accelerometers, gyroscopes, magnetometer, etc.), navigation sensors and systems (e.g., GPS, etc.), and other ranging, imaging, and/or object-detecting sensors. The sensors may be disposed in an interior space 150 of the vehicle 100 and/or on an outside of the vehicle 100. In some embodiments, the sensors and systems may be disposed in one or more portions of a vehicle 100 (e.g., the frame 104, a body panel, a compartment, etc.).

The vehicle sensors and systems may be selected and/or configured to suit a level of operation associated with the vehicle 100. Among other things, the number of sensors used in a system may be altered to increase or decrease information available to a vehicle control system (e.g., affecting control capabilities of the vehicle 100). Additionally or alternatively, the sensors and systems may be part of one or more advanced driver assistance systems (ADAS) associated with a vehicle 100. In any event, the sensors and systems may be used to provide driving assistance at any level of operation (e.g., from fully-manual to fully-autonomous operations, etc.) as described herein.

The various levels of vehicle control and/or operation can be described as corresponding to a level of autonomy associated with a vehicle 100 for vehicle driving operations. For instance, at Level 0, or fully-manual driving operations, a driver (e.g., a human driver) may be responsible for all the driving control operations (e.g., steering, accelerating, braking, etc.) associated with the vehicle. Level 0 may be referred to as a "No Automation" level. At Level 1, the vehicle may be responsible for a limited number of the driving operations associated with the vehicle, while the driver is still responsible for most driving control operations. An example of a Level 1 vehicle may include a vehicle in which the throttle control and/or braking operations may be controlled by the vehicle (e.g., cruise control operations, etc.). Level 1 may be referred to as a "Driver Assistance" level. At Level 2, the vehicle may collect information (e.g., via one or more driving assistance systems, sensors, etc.) about an environment of the vehicle (e.g., surrounding area, roadway, traffic, ambient conditions, etc.) and use the collected information to control driving operations (e.g., steering, accelerating, braking, etc.) associated with the vehicle. In a Level 2 autonomous vehicle, the driver may be required to perform other aspects of driving operations not controlled by the vehicle. Level 2 may be referred to as a "Partial Automation" level. It should be appreciated that Levels 0-2 all involve the driver monitoring the driving operations of the vehicle.

At Level 3, the driver may be separated from controlling all the driving operations of the vehicle except when the vehicle makes a request for the operator to act or intervene in controlling one or more driving operations. In other words, the driver may be separated from controlling the vehicle unless the driver is required to take over for the vehicle. Level 3 may be referred to as a "Conditional Automation" level. At Level 4, the driver may be separated from controlling all the driving operations of the vehicle and the vehicle may control driving operations even when a user fails to respond to a request to intervene. Level 4 may be referred to as a "High Automation" level. At Level 5, the vehicle can control all the driving operations associated with the vehicle in all driving modes. The vehicle in Level 5 may continually monitor traffic, vehicular, roadway, and/or environmental conditions while driving the vehicle. In Level 5, there is no human driver interaction required in any driving mode. Accordingly, Level 5 may be referred to as a "Full Automation" level. It should be appreciated that in Levels 3-5 the vehicle, and/or one or more automated driving systems associated with the vehicle, monitors the driving operations of the vehicle and the driving environment.

As shown in FIG. 1, the vehicle 100 may, for example, include at least one of a ranging and imaging system 112 (e.g., LIDAR, etc.), an imaging sensor 116A, 116F (e.g., camera, IR, etc.), radio object-detection and ranging system sensors 116B (e.g., RADAR, RF, etc.), ultrasonic sensors 116C, and/or other object-detection sensors 116D, 116E. In some embodiments, the LIDAR system 112 and/or sensors may be mounted on a roof 130 of the vehicle 100. In one embodiment, the RADAR sensors 116B may be disposed at least at a front 110, aft 120, or side 160 of the vehicle 100. Among other things, the RADAR sensors may be used to monitor and/or detect a position of other vehicles, pedestrians, and/or other objects near, or proximal to, the vehicle 100. While shown associated with one or more areas of a vehicle 100, it should be appreciated that any of the sensors and systems 116A-K, 112 illustrated in FIGS. 1 and 2 may be disposed in, on, and/or about the vehicle 100 in any position, area, and/or zone of the vehicle 100.

Figure 2:
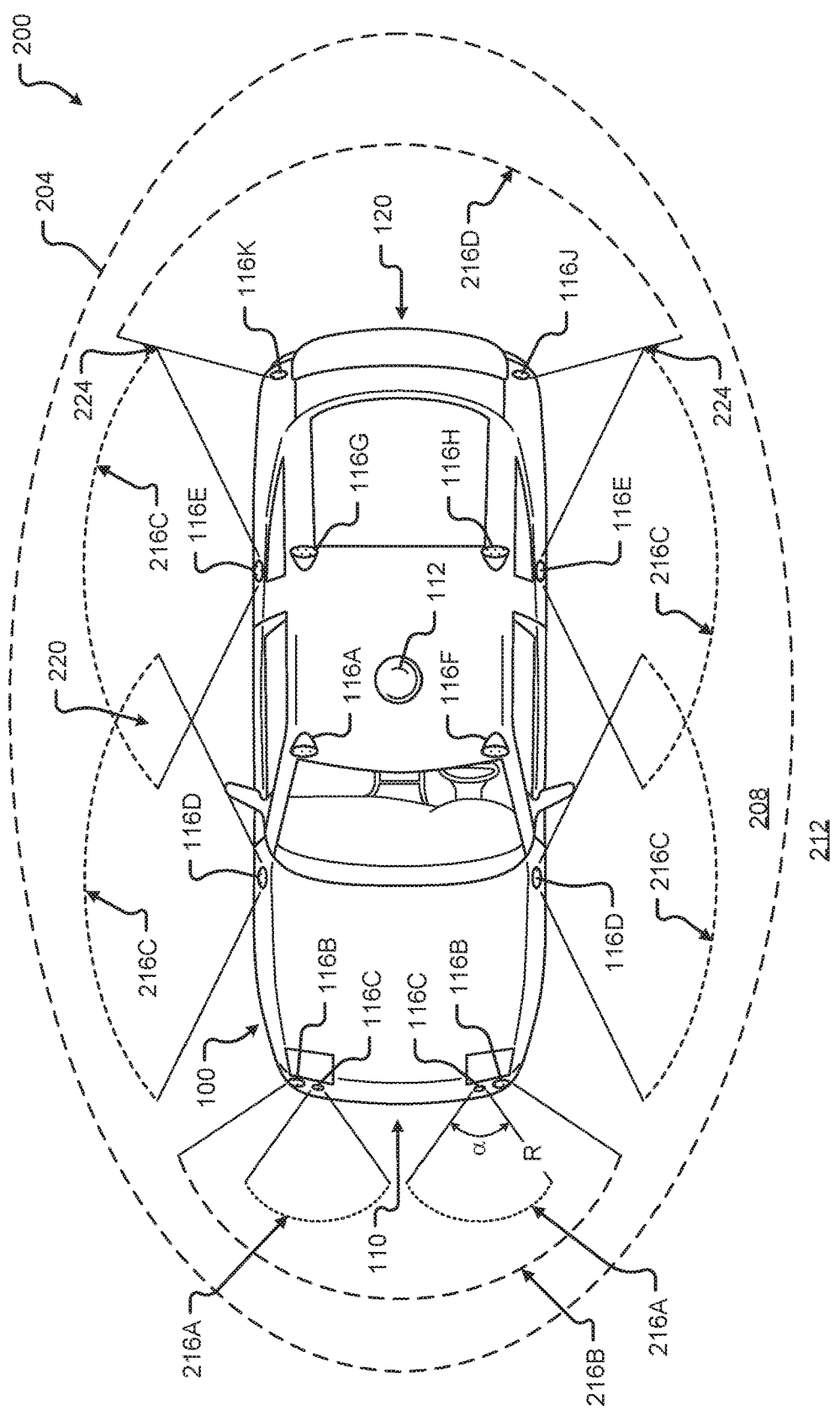
FIG. 2 shows a plan view of the vehicle in accordance with at least some embodiments of the present disclosure.

Referring now to FIG. 2, a plan view of a vehicle 100 will be described in accordance with embodiments of the present disclosure. In particular, FIG. 2 shows a vehicle sensing environment 200 at least partially defined by the sensors and systems 116A-K, 112 disposed in, on, and/or about the vehicle 100. Each sensor 116A-K may include an operational detection range R and operational detection angle $\alpha$. The operational detection range R may define the effective detection limit, or distance, of the sensor 116A-K. In some cases, this effective detection limit may be defined as a distance from a portion of the sensor 116A-K (e.g., a lens, sensing surface, etc.) to a point in space offset from the sensor 116A-K. The effective detection limit may define a distance, beyond which, the sensing capabilities of the sensor 116A-K deteriorate, fail to work, or are unreliable. In some embodiments, the effective detection limit may define a distance, within which, the sensing capabilities of the sensor 116A-K are able to provide accurate and/or reliable detection information. The operational detection angle $\alpha$ may define at least one angle of a span, or between horizontal and/or vertical limits, of a sensor 116A-K. As can be appreciated, the operational detection limit and the operational detection angle $\alpha$ of a sensor 116A-K together may define the effective detection zone 216A-D (e.g., the effective detection area, and/or volume, etc.) of a sensor 116A-K.

In some embodiments, the vehicle 100 may include a ranging and imaging system 112 such as LIDAR, or the like. The ranging and imaging system 112 may be configured to detect visual information in an environment surrounding the vehicle 100. The visual information detected in the environment surrounding the ranging and imaging system 112 may be processed (e.g., via one or more sensor and/or system processors, etc.) to generate a complete 360-degree view of an environment 200 around the vehicle. The ranging and imaging system 112 may be configured to generate changing 360-degree views of the environment 200 in real time, for instance, as the vehicle 100 drives. In some cases, the ranging and imaging system 112 may have an effective detection limit 204 that is some distance from the center of the vehicle 100 outward over 360 degrees. The effective detection limit 204 of the ranging and imaging system 112 defines a view zone 208 (e.g., an area and/or volume, etc.) surrounding the vehicle 100. Any object falling outside of the view zone 208 is in the undetected zone 212 and would not be detected by the ranging and imaging system 112 of the vehicle 100.

Sensor data and information may be collected by one or more sensors or systems 116A-K, 112 of the vehicle 100 monitoring the vehicle sensing environment 200. This information may be processed (e.g., via a processor, computer-vision system, etc.) to determine targets (e.g., objects, signs, people, markings, roadways, conditions, etc.) inside one or more detection zones 208, 216A-D associated with the vehicle sensing environment 200. In some cases, information from multiple sensors 116A-K may be processed to form composite sensor detection information. For example, a first sensor 116A and a second sensor 116F may correspond to a first camera 116A and a second camera 116F aimed in a forward traveling direction of the vehicle 100. In this example, images collected by the cameras 116A, 116F may be combined to form stereo image information. This composite information may increase the capabilities of a single sensor in the one or more sensors 116A-K by, for example, adding the ability to determine depth associated with targets in the one or more detection zones 208, 216A-D. Similar image data may be collected by rear view cameras (e.g., sensors 116G, 116H) aimed in a rearward traveling direction of the vehicle 100.

In some embodiments, multiple sensors 116A-K may be effectively joined to increase a sensing zone and provide increased sensing coverage. For instance, multiple RADAR sensors 116B disposed on the front 110 of the vehicle may be joined to provide a zone 216B of coverage that spans across an entirety of the front 110 of the vehicle. In some cases, the multiple RADAR sensors 116B may cover a detection zone 216B that includes one or more other sensor detection zones 216A. These overlapping detection zones may provide redundant sensing, enhanced sensing, and/or provide greater detail in sensing within a particular portion (e.g., zone 216A) of a larger zone (e.g., zone 216B). Additionally or alternatively, the sensors 116A-K of the vehicle 100 may be arranged to create a complete coverage, via one or more sensing zones 208, 216A-D around the vehicle 100. In some areas, the sensing zones 216C of two or more sensors 116D, 116E may intersect at an overlap zone 220. In some areas, the angle and/or detection limit of two or more sensing zones 216C, 216D (e.g., of two or more sensors 116E, 116J, 116K) may meet at a virtual intersection point 224.

The vehicle 100 may include a number of sensors 116E, 116G, 116H, 116J, 116K disposed proximal to the rear 120 of the vehicle 100. These sensors can include, but are in no way limited to, an imaging sensor, camera, IR, a radio object-detection and ranging sensors, RADAR, RF, ultrasonic sensors, and/or other object-detection sensors. Among other things, these sensors 116E, 116G, 116H, 116J, 116K may detect targets near or approaching the rear 120 of the vehicle 100. For example, another vehicle approaching the rear 120 of the vehicle 100 may be detected by one or more of the ranging and imaging system (e.g., LIDAR) 112, rear-view cameras 116G, 116H, and/or rear facing RADAR sensors 116J, 116K. As described above, the images from the rear-view cameras 116G, 116H may be processed to generate a stereo view (e.g., providing depth associated with an object or environment, etc.) for targets visible to both cameras 116G, 116H. As another example, the vehicle 100 may be driving and one or more of the ranging and imaging system 112, front-facing cameras 116A, 116F, front-facing RADAR sensors 116B, and/or ultrasonic sensors 116C may detect targets in front of the vehicle 100. This approach may provide critical sensor information to a vehicle control system in at least one of the autonomous driving levels described above. For instance, when the vehicle 100 is driving autonomously (e.g., Level 3, Level 4, or Level 5) and detects other vehicles stopped in a travel path, the sensor detection information may be sent to the vehicle control system of the vehicle 100 to control a driving operation (e.g., braking, decelerating, etc.) associated with the vehicle 100 (in this example, slowing the vehicle 100 as to avoid colliding with the stopped other vehicles). As yet another example, the vehicle 100 may be operating and one or more of the ranging and imaging system 112, and/or the side-facing sensors 116D, 116E (e.g., RADAR, ultrasonic, camera, combinations thereof, and/or other type of sensor), may detect targets at a side of the vehicle 100. It should be appreciated that the sensors 116A-K may detect a target that is both at a side 160 and a front 110 of the vehicle 100 (e.g., disposed at a diagonal angle to a centerline of the vehicle 100 running from the front 110 of the vehicle 100 to the rear 120 of the vehicle). Additionally or alternatively, the sensors 116A-K may detect a target that is both, or simultaneously, at a side 160 and a rear 120 of the vehicle 100 (e.g., disposed at a diagonal angle to the centerline of the vehicle 100).

Figure 3:
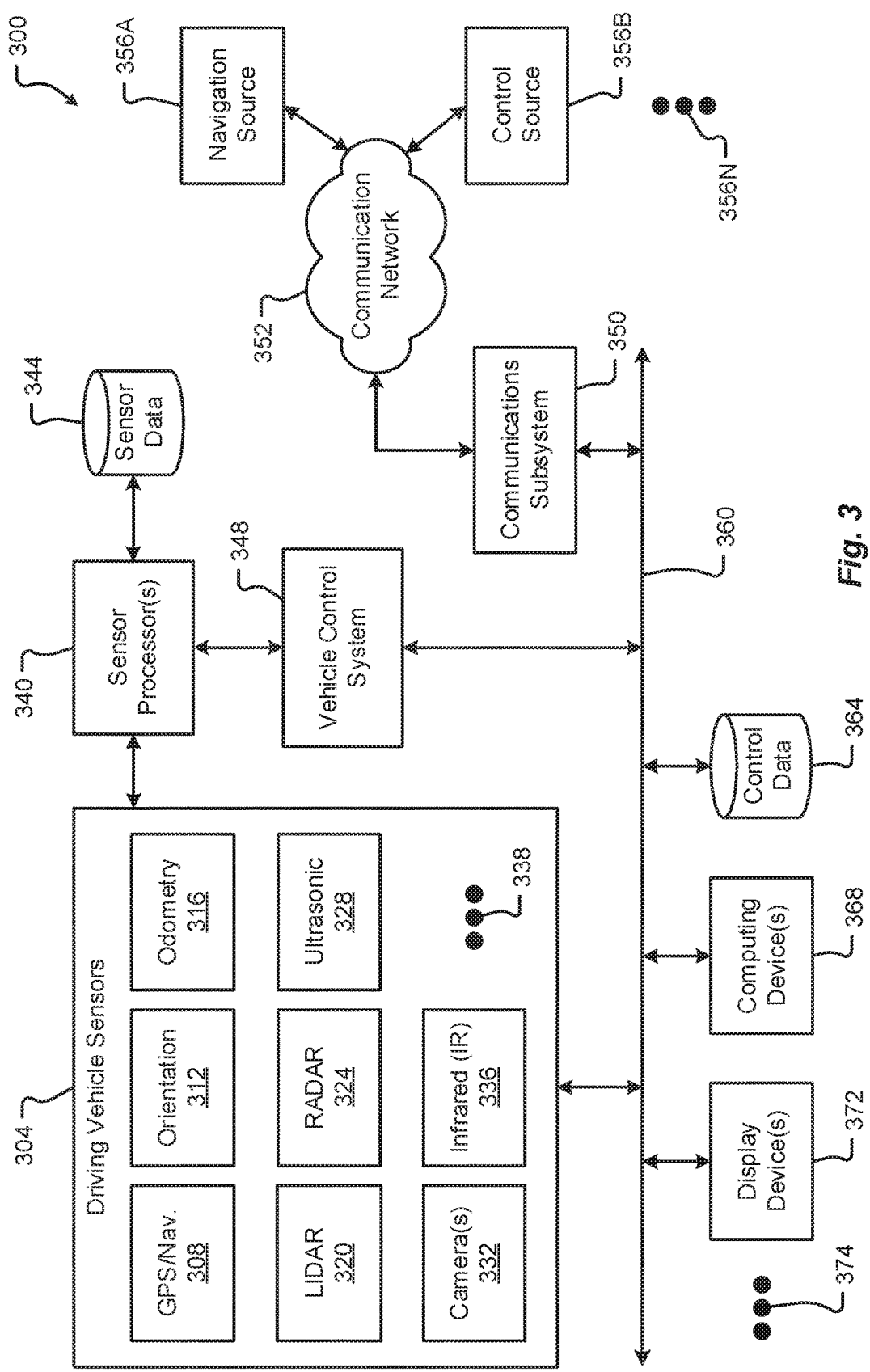
FIG. 3 is a block diagram of an embodiment of a communication environment of the vehicle in accordance with embodiments of the present disclosure.

FIG. 3 is a block diagram of an embodiment of a communication environment 300 of the vehicle 100 in accordance with embodiments of the present disclosure. The communication system 300 may include one or more driving vehicle sensors and systems 304, sensor processors 340, sensor data memory 344, vehicle control system 348, communications subsystem 350, control data 364, computing devices 368, display devices 372, and other components 374 that may be associated with a vehicle 100. These associated components may be electrically and/or communicatively coupled to one another via at least one bus 360. In some embodiments, the one or more associated components may send and/or receive signals across a communication network 352 to at least one of a navigation source 356A, a control source 356B, or some other entity 356N.

In accordance with at least some embodiments of the present disclosure, the communication network 352 may comprise any type of known communication medium or collection of communication media and may use any type of protocols, such as SIP, TCP/IP, SNA, IPX, AppleTalk, and the like, to transport messages between endpoints. The communication network 352 may include wired and/or wireless communication technologies. The Internet is an example of the communication network 352 that constitutes an Internet Protocol (IP) network consisting of many computers, computing networks, and other communication devices located all over the world, which are connected through many telephone systems and other means. Other examples of the communication network 104 include, without limitation, a standard Plain Old Telephone System (POTS), an Integrated Services Digital Network (ISDN), the Public Switched Telephone Network (PSTN), a Local Area Network (LAN), such as an Ethernet network, a Token-Ring network and/or the like, a Wide Area Network (WAN), a virtual network, including without limitation a virtual private network ("VPN"); the Internet, an intranet, an extranet, a cellular network, an infra-red network; a wireless network (e.g., a network operating under any of the IEEE 802.9 suite of protocols, the Bluetooth® protocol known in the art, and/or any other wireless protocol), and any other type of packet-switched or circuit-switched network known in the art and/or any combination of these and/or other networks. In addition, it can be appreciated that the communication network 352 need not be limited to any one network type, and instead may be comprised of a number of different networks and/or network types. The communication network 352 may comprise a number of different communication media such as coaxial cable, copper cable/wire, fiber-optic cable, antennas for transmitting/receiving wireless messages, and combinations thereof.

Alternatively, or in addition, the communication network 352 may include a dedicated short range communication (DSCR) system that enables vehicle-to-vehicle (V2V) communication. DSRC (Dedicated Short Range Communications) provides two-way short-to-medium-range wireless communications capability that permits very high data transmission critical in communications-based active safety applications. In Report and Order FCC-03-324, incorporated herein by reference, the Federal Communications Commission (FCC) allocated 75 MHz of spectrum in the 5.9 GHz band for use by Intelligent Transportations Systems (ITS) vehicle safety and mobility applications. DSRC and other wireless communications technologies help to ensure safe, interoperable connectivity to help prevent vehicular crashes of all types and to enhance mobility and environmental benefits across all transportation system modes. Vehicle safety applications that use vehicle-to-vehicle (V2V) and vehicle-to-infrastructure (V2I) communications may utilize a secure, wireless interface that is dependable in extreme weather conditions and has short time delays facilitated by DSRC. The communication network 352 may be interoperable with protocols related to 802.11p and/or DSRC.

The communication network 352 may not require high bandwidth forms of communication; however, the communication network 352 may require, or place great emphasis on, low latency (e.g. <1 ms) forms of communication to control a vehicle in motion. Therefore, the communication network 352 would need to provide data with a command response time being close to zero; such response time would be important for the safe operation of vehicles if V2V applications are being utilized. Thus, the communication network 352 may utilize one or more networks implementing 5G. As a fully 'driverless' car would need to be driverless in all geographies, full road network coverage with 100% reliability to be a critical element in a driverless car implementation.

The driving vehicle sensors and systems 304 may include at least one navigation 308 (e.g., global positioning system (GPS), etc.), orientation 312, odometry 316, LIDAR 320, RADAR 324, ultrasonic 328, camera 332, infrared (IR) 336, and/or other sensor or system 338. These driving vehicle sensors and systems 304 may be similar, if not identical, to the sensors and systems 116A-K, 112 described in conjunction with FIGS. 1 and 2.

The navigation sensor 308 may include one or more sensors having receivers and antennas that are configured to utilize a satellite-based navigation system including a network of navigation satellites capable of providing geolocation and time information to at least one component of the vehicle 100. Examples of the navigation sensor 308 as described herein may include, but are not limited to, at least one of Garmin® GLO™ family of GPS and GLONASS combination sensors, Garmin® GPS 15x™ family of sensors, Garmin® GPS 16x™ family of sensors with high-sensitivity receiver and antenna, Garmin® GPS 18x OEM family of high-sensitivity GPS sensors, Dewetron DEWE-VGPS series of GPS sensors, GlobalSat 1-Hz series of GPS sensors, other industry-equivalent navigation sensors and/or systems, and may perform navigational and/or geolocation functions using any known or future-developed standard and/or architecture.

The orientation sensor 312 may include one or more sensors configured to determine an orientation of the vehicle 100 relative to at least one reference point. In some embodiments, the orientation sensor 312 may include at least one pressure transducer, stress/strain gauge, accelerometer, gyroscope, and/or geomagnetic sensor. Examples of the navigation sensor 308 as described herein may include, but are not limited to, at least one of Bosch Sensortec BMX 160 series low-power absolute orientation sensors, Bosch Sensortec BMX055 9-axis sensors, Bosch Sensortec BMI055 6-axis inertial sensors, Bosch Sensortec BMI160 6-axis inertial sensors, Bosch Sensortec BNIF055 9-axis inertial sensors (accelerometer, gyroscope, and magnetometer) with integrated Cortex M0+ microcontroller, Bosch Sensortec BMP280 absolute barometric pressure sensors, Infineon TLV493D-A1B6 3D magnetic sensors, Infineon TLI493D-W1B6 3D magnetic sensors, Infineon TL family of 3D magnetic sensors, Murata Electronics SCC2000 series combined gyro sensor and accelerometer, Murata Electronics SCC1300 series combined gyro sensor and accelerometer, other industry-equivalent orientation sensors and/or systems, and may perform orientation detection and/or determination functions using any known or future-developed standard and/or architecture.

The odometry sensor and/or system 316 may include one or more components that is configured to determine a change in position of the vehicle 100 over time. In some embodiments, the odometry system 316 may utilize data from one or more other sensors and/or systems 304 in determining a position (e.g., distance, location, etc.) of the vehicle 100 relative to a previously measured position for the vehicle 100. Additionally or alternatively, the odometry sensors 316 may include one or more encoders, Hall speed sensors, and/or other measurement sensors/devices configured to measure a wheel speed, rotation, and/or number of revolutions made over time. Examples of the odometry sensor/system 316 as described herein may include, but are not limited to, at least one of Infineon TLE4924/26/27/28C high-performance speed sensors, Infineon TL4941plusC(B) single chip differential Hall wheel-speed sensors, Infineon TL5041plusC Giant Mangnetoresistance (GMR) effect sensors, Infineon TL family of magnetic sensors, EPC Model 25SP Accu-CoderPro™ incremental shaft encoders, EPC Model 30M compact incremental encoders with advanced magnetic sensing and signal processing technology, EPC Model 925 absolute shaft encoders, EPC Model 958 absolute shaft encoders, EPC Model MA36S/MA63S/SA36S absolute shaft encoders, Dynapar™ F18 commutating optical encoder, Dynapar™ HS35R family of phased array encoder sensors, other industry-equivalent odometry sensors and/or systems, and may perform change in position detection and/or determination functions using any known or future-developed standard and/or architecture.

The LIDAR sensor/system 320 may include one or more components configured to measure distances to targets using laser illumination. In some embodiments, the LIDAR sensor/system 320 may provide 3D imaging data of an environment around the vehicle 100. The imaging data may be processed to generate a full 360-degree view of the environment around the vehicle 100. The LIDAR sensor/system 320 may include a laser light generator configured to generate a plurality of target illumination laser beams (e.g., laser light channels). In some embodiments, this plurality of laser beams may be aimed at, or directed to, a rotating reflective surface (e.g., a mirror) and guided outwardly from the LIDAR sensor/system 320 into a measurement environment. The rotating reflective surface may be configured to continually rotate 360 degrees about an axis, such that the plurality of laser beams is directed in a full 360-degree range around the vehicle 100. A photodiode receiver of the LIDAR sensor/system 320 may detect when light from the plurality of laser beams emitted into the measurement environment returns (e.g., reflected echo) to the LIDAR sensor/system 320. The LIDAR sensor/system 320 may calculate, based on a time associated with the emission of light to the detected return of light, a distance from the vehicle 100 to the illuminated target. In some embodiments, the LIDAR sensor/system 320 may generate over 2.0 million points per second and have an effective operational range of at least 100 meters. Examples of the LIDAR sensor/system 320 as described herein may include, but are not limited to, at least one of Velodyne® LiDAR™ HDL-64E 64-channel LIDAR sensors, Velodyne® LiDAR™ HDL-32E 32-channel LIDAR sensors, Velodyne® LiDAR™ PUCK™ VLP-16 16-channel LIDAR sensors, Leica Geosystems Pegasus: Two mobile sensor platform, Garmin® LIDAR-Lite v3 measurement sensor, Quanergy M8 LiDAR sensors, Quanergy S3 solid state LiDAR sensor, LeddarTech® LeddarVU compact solid state fixed-beam LIDAR sensors, other industry-equivalent LIDAR sensors and/or systems, and may perform illuminated target and/or obstacle detection in an environment around the vehicle 100 using any known or future-developed standard and/or architecture.

The RADAR sensors 324 may include one or more radio components that are configured to detect objects/targets in an environment of the vehicle 100. In some embodiments, the RADAR sensors 324 may determine a distance, position, and/or movement vector (e.g., angle, speed, etc.) associated with a target over time. The RADAR sensors 324 may include a transmitter configured to generate and emit electromagnetic waves (e.g., radio, microwaves, etc.) and a receiver configured to detect returned electromagnetic waves. In some embodiments, the RADAR sensors 324 may include at least one processor configured to interpret the returned electromagnetic waves and determine locational properties of targets. Examples of the RADAR sensors 324 as described herein may include, but are not limited to, at least one of Infineon RASIC™ RTN7735PL transmitter and RRN7745PL/46PL receiver sensors, Autoliv ASP Vehicle RADAR sensors, Delphi L2C0051TR 77 GHz ESR Electronically Scanning Radar sensors, Fujitsu Ten Ltd. Automotive Compact 77 GHz 3D Electronic Scan Millimeter Wave Radar sensors, other industry-equivalent RADAR sensors and/or systems, and may perform radio target and/or obstacle detection in an environment around the vehicle 100 using any known or future-developed standard and/or architecture. Further, the radar sensors 324 may employ Short Range Radar (SRR) technology operating at 24 GHz and/or multi-range radar (MRR) operating at 79 GHz. The 79 GHz radar enables the detection of pedestrians and the like around vehicles which have proved to be more difficult to be detect by 77 GHz band radar.

The radar sensor(s) 324 may be capable of operating at the four major frequency bands allocated for radar applications, each of which may be divided into two sub-categories: 24-GHz band and 77-GHz band. The 24-GHz band consists of two bands, one around 24.125 GHz with a bandwidth of around 200 MHz and, the other around 24 GHz with a bandwidth of 5 GHz. Both of these bands may be used for short/mid-range radars. The 77-GHz band also consists of two sub-bands, 76-77 GHz for narrow-band long-range radar and 77-81 GHz for short-range wideband radar. As frequency increases, smaller antenna size may be employed and higher angular resolution may be achieved. Furthermore, by increasing the carrier frequency, the Doppler frequency also increases proportional to the velocity of the target; hence by using mm-wave frequencies, a higher speed resolution can be achieved. Range resolution depends on the modulated signal bandwidth, thus wideband radars can achieve a higher range resolution, which is required in short-range radar applications. By using the 77-GHz band for long-range and short-range applications, the same semiconductor technology solutions may be used in the implementation of both of them. Also, higher output power is allowed in this band, as compared to the 24-GHz radar band.

76-77-GHz and 77-81-GHz radar sensors together are capable of satisfying the requirements of automotive radar systems including short-range and long-range object detection. For short-range radar applications, the resolution may be high; as a result, a wide bandwidth is required. Therefore, the 77-81-GHz band is allocated for short-range radar (30-50 m). For long-range adaptive cruise control, a lower resolution is sufficient; as a result, a narrower bandwidth can be used. The 76-77-GHz is allocated for this application.

The ultrasonic sensors 328 may include one or more components that are configured to detect objects/targets in an environment of the vehicle 100. In some embodiments, the ultrasonic sensors 328 may determine a distance, position, and/or movement vector (e.g., angle, speed, etc.) associated with a target over time. The ultrasonic sensors 328 may include an ultrasonic transmitter and receiver, or transceiver, configured to generate and emit ultrasound waves and interpret returned echoes of those waves. In some embodiments, the ultrasonic sensors 328 may include at least one processor configured to interpret the returned ultrasonic waves and determine locational properties of targets. Examples of the ultrasonic sensors 328 as described herein may include, but are not limited to, at least one of Texas Instruments TIDA-00151 automotive ultrasonic sensor interface IC sensors, MaxBotix® MB8450 ultrasonic proximity sensor, MaxBotix® ParkSonar™-EZ ultrasonic proximity sensors, Murata Electronics MA40H1S-R open-structure ultrasonic sensors, Murata Electronics MA40S4R/S open-structure ultrasonic sensors, Murata Electronics MA58MF14-7N waterproof ultrasonic sensors, other industry-equivalent ultrasonic sensors and/or systems, and may perform ultrasonic target and/or obstacle detection in an environment around the vehicle 100 using any known or future-developed standard and/or architecture.

The camera sensors 332 may include one or more components configured to detect image information associated with an environment of the vehicle 100. In some embodiments, the camera sensors 332 may include a lens, filter, image sensor, and/or a digital image processer. It is an aspect of the present disclosure that multiple camera sensors 332 may be used together to generate stereo images providing depth measurements. Examples of the camera sensors 332 as described herein may include, but are not limited to, at least one of ON Semiconductor® MT9V024 Global Shutter VGA GS CMOS image sensors, Teledyne DALSA Falcon2 camera sensors, CMOSIS CMV50000 high-speed CMOS image sensors, other industry-equivalent camera sensors and/or systems, and may perform visual target and/or obstacle detection in an environment around the vehicle 100 using any known or future-developed standard and/or architecture.

The infrared (IR) sensors 336 may include one or more components configured to detect image information associated with an environment of the vehicle 100. The IR sensors 336 may be configured to detect targets in low-light, dark, or poorly-lit environments. The IR sensors 336 may include an IR light emitting element (e.g., IR light emitting diode (LED), etc.) and an IR photodiode. In some embodiments, the IR photodiode may be configured to detect returned IR light at or about the same wavelength to that emitted by the IR light emitting element. In some embodiments, the IR sensors 336 may include at least one processor configured to interpret the returned IR light and determine locational properties of targets. The IR sensors 336 may be configured to detect and/or measure a temperature associated with a target (e.g., an object, pedestrian, other vehicle, etc.). Examples of IR sensors 336 as described herein may include, but are not limited to, at least one of Opto Diode lead-salt IR array sensors, Opto Diode OD-850 Near-IR LED sensors, Opto Diode SA/SHA727 steady state IR emitters and IR detectors, FLIR® LS microbolometer sensors, FLIR® TacFLIR 380-HD InSb MWIR FPA and HD MWIR thermal sensors, FLIR® VOx 640×480 pixel detector sensors, Delphi IR sensors, other industry-equivalent IR sensors and/or systems, and may perform IR visual target and/or obstacle detection in an environment around the vehicle 100 using any known or future-developed standard and/or architecture.

In some embodiments, the driving vehicle sensors and systems 304 may include other sensors 338 and/or combinations of the sensors 308-336 described above. Additionally or alternatively, one or more of the sensors 308-336 described above may include one or more processors configured to process and/or interpret signals detected by the one or more sensors 308-336. In some embodiments, the processing of at least some sensor information provided by the vehicle sensors and systems 304 may be processed by at least one sensor processor 340. Raw and/or processed sensor data may be stored in a sensor data memory 344 storage medium. In some embodiments, the sensor data memory 344 may store instructions used by the sensor processor 340 for processing sensor information provided by the sensors and systems 304. In any event, the sensor data memory 344 may be a disk drive, optical storage device, solid-state storage device such as a random access memory ("RAM") and/or a read-only memory ("ROM"), which can be programmable, flash-updateable, and/or the like.

The vehicle control system 348 may receive processed sensor information from the sensor processor 340 and determine to control an aspect of the vehicle 100. Controlling an aspect of the vehicle 100 may include presenting information via one or more display devices 372 associated with the vehicle 100, sending commands to one or more computing devices 368 associated with the vehicle 100, and/or controlling a driving operation of the vehicle 100. In some embodiments, the vehicle control system 348 may correspond to one or more computing systems that control driving operations of the vehicle 100 in accordance with the Levels of driving autonomy described above. In one embodiment, the vehicle control system 348 may operate a speed of the vehicle 100 by controlling an output signal to the accelerator and/or braking system of the vehicle. In this example, the vehicle control system 348 may receive sensor data describing an environment surrounding the vehicle 100 and, based on the sensor data received, determine to adjust the acceleration, power output, and/or braking of the vehicle 100. The vehicle control system 348 may additionally control steering and/or other driving functions of the vehicle 100.

The vehicle control system 348 may communicate, in real time, with the driving sensors and systems 304 forming a feedback loop. In particular, upon receiving sensor information describing a condition of targets in the environment surrounding the vehicle 100, the vehicle control system 348 may autonomously make changes to a driving operation of the vehicle 100. The vehicle control system 348 may then receive subsequent sensor information describing any change to the condition of the targets detected in the environment as a result of the changes made to the driving operation. This continual cycle of observation (e.g., via the sensors, etc.) and action (e.g., selected control or non-control of vehicle operations, etc.) allows the vehicle 100 to operate autonomously in the environment.

In some embodiments, the one or more components of the vehicle 100 (e.g., the driving vehicle sensors 304, vehicle control system 348, display devices 372, etc.) may communicate across the communication network 352 to one or more entities 356A-N via a communications subsystem 350 of the vehicle 100. Embodiments of the communications subsystem 350 are described in greater detail in conjunction with FIG. 5. For instance, the navigation sensors 308 may receive global positioning, location, and/or navigational information from a navigation source 356A. In some embodiments, the navigation source 356A may be a global navigation satellite system (GNSS) similar, if not identical, to NAVSTAR GPS, GLONASS, EU Galileo, and/or the BeiDou Navigation Satellite System (BDS) to name a few.

In some embodiments, the vehicle control system 348 may receive control information from one or more control sources 356B. The control source 356B may provide vehicle control information including autonomous driving control commands, vehicle operation override control commands, and the like. The control source 356B may correspond to an autonomous vehicle control system, a traffic control system, an administrative control entity, and/or some other controlling server. It is an aspect of the present disclosure that the vehicle control system 348 and/or other components of the vehicle 100 may exchange communications with the control source 356B across the communication network 352 and via the communications subsystem 350.

Information associated with controlling driving operations of the vehicle 100 may be stored in a control data memory 364 storage medium. The control data memory 364 may store instructions used by the vehicle control system 348 for controlling driving operations of the vehicle 100, historical control information, autonomous driving control rules, and the like. In some embodiments, the control data memory 364 may be a disk drive, optical storage device, solid-state storage device such as a random access memory ("RAM") and/or a read-only memory ("ROM"), which can be programmable, flash-updateable, and/or the like.

In addition to the mechanical components described herein, the vehicle 100 may include a number of user interface devices. The user interface devices receive and translate human input into a mechanical movement or electrical signal or stimulus. The human input may be one or more of motion (e.g., body movement, body part movement, in two-dimensional or three-dimensional space, etc.), voice, touch, and/or physical interaction with the components of the vehicle 100. In some embodiments, the human input may be configured to control one or more functions of the vehicle 100 and/or systems of the vehicle 100 described herein. User interfaces may include, but are in no way limited to, at least one graphical user interface of a display device, steering wheel or mechanism, transmission lever or button (e.g., including park, neutral, reverse, and/or drive positions, etc.), throttle control pedal or mechanism, brake control pedal or mechanism, power control switch, communications equipment, etc.

Figure 4:
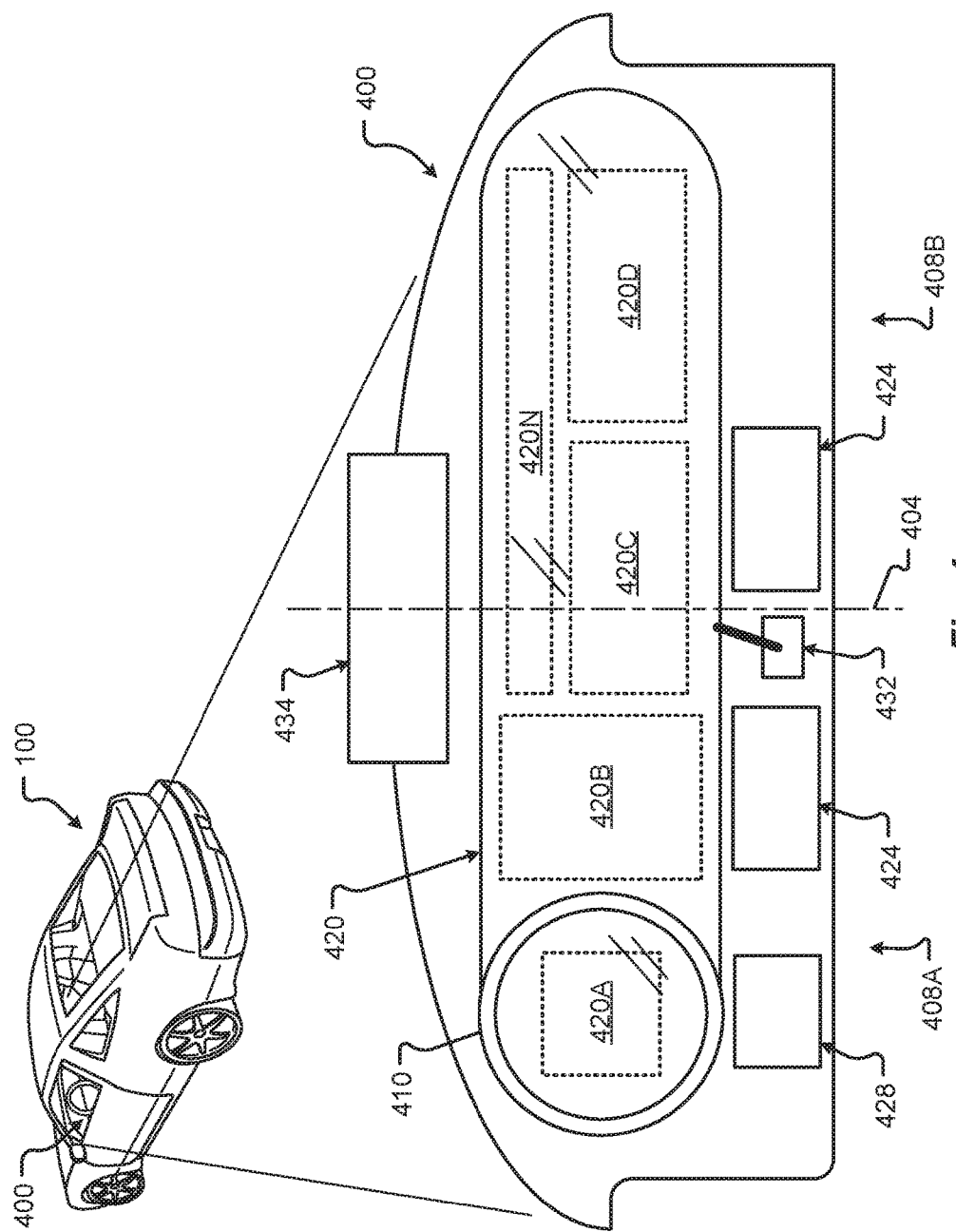
FIG. 4 shows an embodiment of the instrument panel of the vehicle according to one embodiment of the present disclosure.

FIG. 4 shows one embodiment of the instrument panel 400 of the vehicle 100. The instrument panel 400 of vehicle 100 comprises a steering wheel 410, a vehicle operational display 420 (e.g., configured to present and/or display driving data such as speed, measured air resistance, vehicle information, entertainment information, etc.), one or more auxiliary displays 424 (e.g., configured to present and/or display information segregated from the operational display 420, entertainment applications, movies, music, etc.), a heads-up display 434 (e.g., configured to display any information previously described including, but in no way limited to, guidance information such as route to destination, or obstacle warning information to warn of a potential collision, or some or all primary vehicle operational data such as speed, resistance, etc.), a power management display 428 (e.g., configured to display data corresponding to electric power levels of vehicle 100, reserve power, charging status, etc.), and an input device 432 (e.g., a controller, touchscreen, or other interface device configured to interface with one or more displays in the instrument panel or components of the vehicle 100. The input device 432 may be configured as a joystick, mouse, touchpad, tablet, 3D gesture capture device, etc.). In some embodiments, the input device 432 may be used to manually maneuver a portion of the vehicle 100 into a charging position (e.g., moving a charging plate to a desired separation distance, etc.).

While one or more of displays of the instrument panel 400 may be touch-screen displays, it should be appreciated that the vehicle operational display may be a display incapable of receiving touch input. For instance, the operational display 420 that spans across an interior space centerline 404 and across both a first zone 408A and a second zone 408B may be isolated from receiving input from touch, especially from a passenger. In some cases, a display that provides vehicle operation or critical systems information and interface may be restricted from receiving touch input and/or be configured as a non-touch display. This type of configuration can prevent dangerous mistakes in providing touch input where such input may cause an accident or unwanted control.

In some embodiments, one or more displays of the instrument panel 400 may be mobile devices and/or applications residing on a mobile device such as a smart phone. Additionally or alternatively, any of the information described herein may be presented to one or more portions 420A-N of the operational display 420 or other display 424, 428, 434. In one embodiment, one or more displays of the instrument panel 400 may be physically separated or detached from the instrument panel 400. In some cases, a detachable display may remain tethered to the instrument panel 400.

The portions 420A-N of the operational display 420 may be dynamically reconfigured and/or resized to suit any display of information as described. Additionally or alternatively, the number of portions 420A-N used to visually present information via the operational display 420 may be dynamically increased or decreased as required, and are not limited to the configurations shown.

Figure 5:
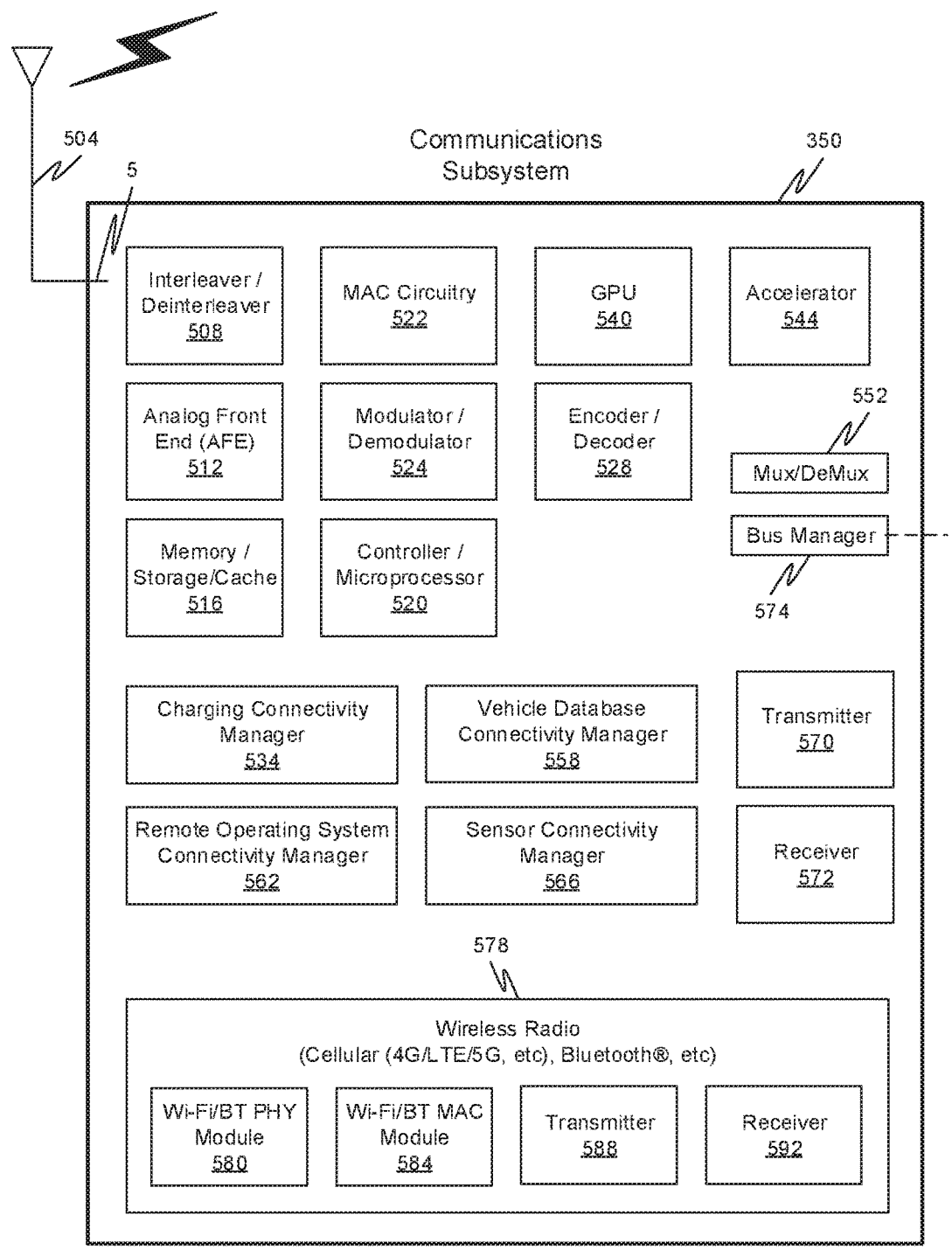
FIG. 5 is a block diagram of an embodiment of a communications subsystem of the vehicle.

FIG. 5 illustrates a hardware diagram of communications componentry that can be optionally associated with the vehicle 100 in accordance with embodiments of the present disclosure.

The communications componentry can include one or more wired or wireless devices such as a transceiver(s) and/or modem that allows communications not only between the various systems disclosed herein but also with other devices, such as devices on a network, and/or on a distributed network such as the Internet and/or in the cloud and/or with other vehicle(s).

The communications subsystem 350 can also include inter- and intra-vehicle communications capabilities such as hotspot and/or access point connectivity for any one or more of the vehicle occupants and/or vehicle-to-vehicle communications.

Additionally, and while not specifically illustrated, the communications subsystem 350 can include one or more communications links (that can be wired or wireless) and/or communications busses (managed by the bus manager 574), including one or more of CANbus, OBD-II, ARCINC 429, Byteflight, CAN (Controller Area Network), D2B (Domestic Digital Bus), FlexRay, DC-BUS, IDB-1394, IEBus, I2C, ISO 9141-1/-2, J1708, J1587, J1850, J1939, ISO 11783, Keyword Protocol 2000, LIN (Local Interconnect Network), MOST (Media Oriented Systems Transport), Multifunction Vehicle Bus, SMARTwireX, SPI, VAN (Vehicle Area Network), DSRC, V2V, V2I, and the like or, in general, any communications protocol and/or standard(s).

The various protocols and communications can be communicated one or more of wirelessly and/or over transmission media such as single wire, twisted pair, fiber optic, IEEE 1394, MIL-STD-1553, MIL-STD-1773, power-line communication, or the like. (All of the above standards and protocols are incorporated herein by reference in their entirety).

As discussed, the communications subsystem 350 enables communications between any of the inter-vehicle systems and subsystems as well as communications with non-collocated resources, such as those reachable over a network such as the Internet.

The communications subsystem 350, in addition to well-known componentry (which has been omitted for clarity), includes interconnected elements including one or more of: one or more antennas 504, an interleaver/deinterleaver 508, an analog front end (AFE) 512, memory/storage/cache 516, controller/microprocessor 520, MAC circuitry 522, modulator/demodulator 524, encoder/decoder 528, a plurality of connectivity managers 534, 558, 562, 566, GPU 540, accelerator 544, a multiplexer/demultiplexer 552, transmitter 570, receiver 572 and wireless radio 578 components such as a Wi-Fi PHY/Bluetooth® module 580, a Wi-Fi/BT MAC module 584, transmitter 588 and receiver 592. The various elements in the device 350 are connected by one or more links/busses 5 (not shown, again for sake of clarity).

The device 350 can have one or more antennas 504, for use in wireless communications such as multi-input multi-output (MIMO) communications, multi-user multi-input multi-output (MU-MIMO) communications Bluetooth®, LTE, 4G, 5G, Near-Field Communication (NFC), DSRC, V2V, V2I etc., and in general for any type of wireless communications. The antenna(s) 504 can include, but are not limited to, one or more of directional antennas, omnidirectional antennas, monopoles, patch antennas, loop antennas, microstrip antennas, dipoles, and any other antenna(s) suitable for communication transmission/reception. In an exemplary embodiment, transmission/reception using MIMO may require particular antenna spacing. In another exemplary embodiment, MIMO transmission/reception can enable spatial diversity allowing for different channel characteristics at each of the antennas. In yet another embodiment, MIMO transmission/reception can be used to distribute resources to multiple users, for example within vehicle 100 and/or in another vehicle.

Antenna(s) 504 generally interact with the Analog Front End (AFE) 512, which is needed to enable the correct processing of the received modulated signal and signal conditioning for a transmitted signal. The AFE 512 can be functionally located between the antenna and a digital baseband system in order to convert the analog signal into a digital signal for processing and vice-versa.

The subsystem 350 can also include a controller/microprocessor 520 and a memory/storage/cache 516. The subsystem 350 can interact with the memory/storage/cache 516, which may store information and operations necessary for configuring and transmitting or receiving the information described herein. The memory/storage/cache 516 may also be used in connection with the execution of application programming or instructions by the controller/microprocessor 520, and for temporary or long-term storage of program instructions and/or data. As examples, the memory/storage/cache 520 may comprise a computer-readable device, RAM, ROM, DRAM, SDRAM, and/or other storage device(s) and media.

The controller/microprocessor 520 may comprise a general purpose programmable processor or controller for executing application programming or instructions related to the subsystem 350. Furthermore, the controller/microprocessor 520 can perform operations for configuring and transmitting/receiving information as described herein. The controller/microprocessor 520 may include multiple processor cores, and/or implement multiple virtual processors. Optionally, the controller/microprocessor 520 may include multiple physical processors. By way of example, the controller/microprocessor 520 may comprise a specially configured Application Specific Integrated Circuit (ASIC) or other integrated circuit, a digital signal processor(s), a controller, a hardwired electronic or logic circuit, a programmable logic device or gate array, a special purpose computer, or the like.

The subsystem 350 can further include a transmitter 570 and receiver 572 which can transmit and receive signals, respectively, to and from other devices, subsystems and/or other destinations using the one or more antennas 504 and/or links/busses. Included in the subsystem 350 circuitry is the medium access control or MAC Circuitry 522. MAC circuitry 522 provides for controlling access to the wireless medium. In an exemplary embodiment, the MAC circuitry 522 may be arranged to contend for the wireless medium and configure frames or packets for communicating over the wired/wireless medium.

The subsystem 350 can also optionally contain a security module (not shown). This security module can contain information regarding, but not limited to, security parameters required to connect the device to one or more other devices or other available network(s), and can include WEP or WPA/WPA-2 (optionally+AES and/or TKIP) security access keys, network keys, etc. The WEP security access key is a security password used by Wi-Fi networks. Knowledge of this code can enable a wireless device to exchange information with an access point and/or another device. The information exchange can occur through encoded messages with the WEP access code often being chosen by the network administrator. WPA is an added security standard that is also used in conjunction with network connectivity with stronger encryption than WEP.

In some embodiments, the communications subsystem 350 also includes a GPU 540, an accelerator 544, a Wi-Fi/BT/BLE PHY module 580 and a Wi-Fi/BT/BLE MAC module 584 and wireless transmitter 588 and receiver 592. In some embodiments, the GPU 540 may be a graphics processing unit, or visual processing unit, comprising at least one circuit and/or chip that manipulates and changes memory to accelerate the creation of images in a frame buffer for output to at least one display device. The GPU 540 may include one or more of a display device connection port, printed circuit board (PCB), a GPU chip, a metal-oxide-semiconductor field-effect transistor (MOSFET), memory (e.g., single data rate random-access memory (SDRAM), double data rate random-access memory (DDR) RAM, etc., and/or combinations thereof), a secondary processing chip (e.g., handling video out capabilities, processing, and/or other functions in addition to the GPU chip, etc.), a capacitor, heatsink, temperature control or cooling fan, motherboard connection, shielding, and the like.

The various connectivity managers 534, 558, 562, 566 manage and/or coordinate communications between the subsystem 350 and one or more of the systems disclosed herein and one or more other devices/systems. The connectivity managers 534, 558, 562, 566 include a charging connectivity manager 534, a vehicle database connectivity manager 558, a remote operating system connectivity manager 562, and a sensor connectivity manager 566.

The charging connectivity manager 534 can coordinate not only the physical connectivity between the vehicle 100 and a charging device/vehicle, but can also communicate with one or more of a power management controller, one or more third parties and optionally a billing system(s). As an example, the vehicle 100 can establish communications with the charging device/vehicle to one or more of coordinate interconnectivity between the two (e.g., by spatially aligning the charging receptacle on the vehicle with the charger on the charging vehicle) and optionally share navigation information. Once charging is complete, the amount of charge provided can be tracked and optionally forwarded to, for example, a third party for billing. In addition to being able to manage connectivity for the exchange of power, the charging connectivity manager 534 can also communicate information, such as billing information to the charging vehicle and/or a third party. This billing information could be, for example, the owner of the vehicle, the driver/occupant(s) of the vehicle, company information, or in general any information usable to charge the appropriate entity for the power received.

The vehicle database connectivity manager 558 allows the subsystem 350 to receive and/or share information stored in the vehicle database. This information can be shared with other vehicle components/subsystems and/or other entities, such as third parties and/or charging systems. The information can also be shared with one or more vehicle occupant devices, such as an app (application) on a mobile device the driver uses to track information about the vehicle 100 and/or a dealer or service/maintenance provider. In general, any information stored in the vehicle database can optionally be shared with any one or more other devices optionally subject to any privacy or confidentiality restrictions.

The remote operating system connectivity manager 562 facilitates communications between the vehicle 100 and any one or more autonomous vehicle systems. These communications can include one or more of navigation information, vehicle information, other vehicle information, weather information, occupant information, or in general any information related to the remote operation of the vehicle 100.

The sensor connectivity manager 566 facilitates communications between any one or more of the vehicle sensors (e.g., the driving vehicle sensors and systems 304, etc.) and any one or more of the other vehicle systems. The sensor connectivity manager 566 can also facilitate communications between any one or more of the sensors and/or vehicle systems and any other destination, such as a service company, app, or in general to any destination where sensor data is needed.

In accordance with one exemplary embodiment, any of the communications discussed herein can be communicated via the conductor(s) used for charging. One exemplary protocol usable for these communications is Power-line communication (PLC). PLC is a communication protocol that uses electrical wiring to simultaneously carry both data, and Alternating Current (AC) electric power transmission or electric power distribution. It is also known as power-line carrier, power-line digital subscriber line (PDSL), mains communication, power-line telecommunications, or power-line networking (PLN). For DC environments in vehicles PLC can be used in conjunction with CAN-bus, LIN-bus over power line (DC-LIN) and DC-BUS.

The communications subsystem 350 can also optionally manage one or more identifiers, such as an IP (Internet protocol) address(es), associated with the vehicle and one or more other systems or subsystems or components therein. These identifiers can be used in conjunction with any one or more of the connectivity managers as discussed herein.

Figure 6:
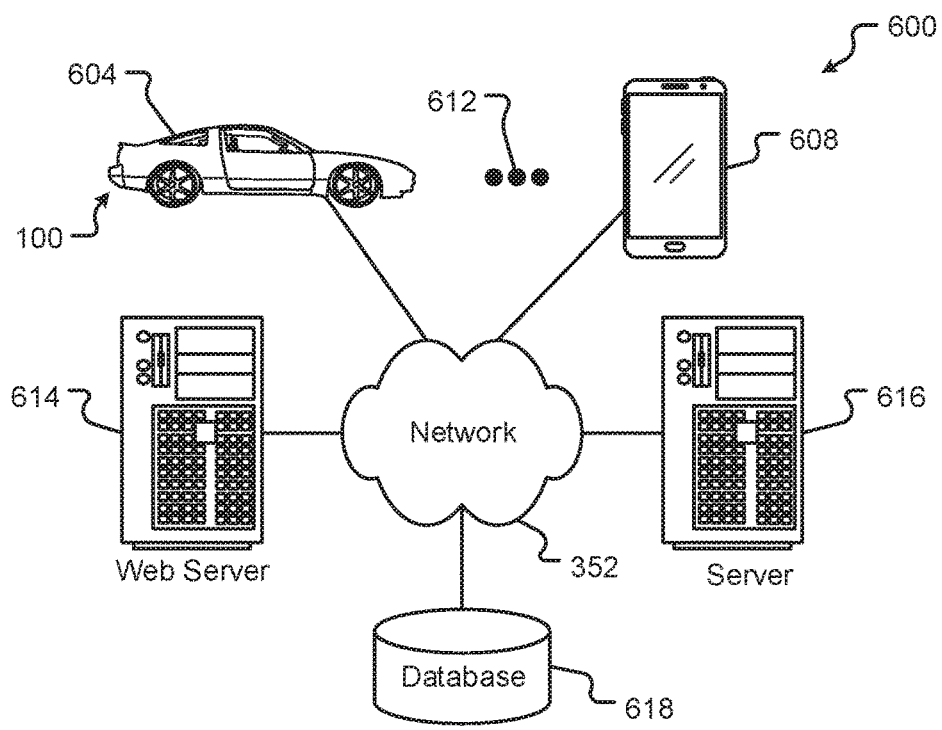
FIG. 6 is a block diagram of a computing environment associated with the embodiments presented herein.

FIG. 6 illustrates a block diagram of a computing environment 600 that may function as the servers, user computers, or other systems provided and described herein. The computing environment 600 includes one or more user computers, or computing devices, such as a vehicle computing device 604, a communication device 608, and/or more 612. The computing devices 604, 608, 612 may include general purpose personal computers (including, merely by way of example, personal computers, and/or laptop computers running various versions of Microsoft Corp.'s Windows® and/or Apple Corp.'s Macintosh® operating systems) and/or workstation computers running any of a variety of commercially-available UNIX® or UNIX-like operating systems. These computing devices 604, 608, 612 may also have any of a variety of applications, including for example, database client and/or server applications, and web browser applications. Alternatively, the computing devices 604, 608, 612 may be any other electronic device, such as a thin-client computer, Internet-enabled mobile telephone, and/or personal digital assistant, capable of communicating via a network 352 and/or displaying and navigating web pages or other types of electronic documents. Although the exemplary computing environment 600 is shown with two computing devices, any number of user computers or computing devices may be supported.

The computing environment 600 may also include one or more servers 614, 616. In this example, server 614 is shown as a web server and server 616 is shown as an application server. The web server 614 may be used to process requests for web pages or other electronic documents from computing devices 604, 608, 612. The web server 614 can be running an operating system including any of those discussed above, as well as any commercially-available server operating systems. The web server 614 can also run a variety of server applications, including SIP (Session Initiation Protocol) servers, HTTP(s) servers, FTP servers, CGI servers, database servers, Java servers, and the like. In some instances, the web server 614 may publish operations available as one or more web services.

The computing environment 600 may also include one or more file and or/application servers 616, which can, in addition to an operating system, include one or more applications accessible by a client running on one or more of the computing devices 604, 608, 612. The server(s) 616 and/or 614 may be one or more general purpose computers capable of executing programs or scripts in response to the computing devices 604, 608, 612. As one example, the server 616, 614 may execute one or more web applications. The web application may be implemented as one or more scripts or programs written in any programming language, such as Java™, C, C#®, or C++, and/or any scripting language, such as Perl, Python, or TCL, as well as combinations of any programming/scripting languages. The application server(s) 616 may also include database servers, including without limitation those commercially available from Oracle®, Microsoft®, Sybase®, IBM® and the like, which can process requests from database clients running on a computing device 604, 608, 612.

The web pages created by the server 614 and/or 616 may be forwarded to a computing device 604, 608, 612 via a web (file) server 614, 616. Similarly, the web server 614 may be able to receive web page requests, web services invocations, and/or input data from a computing device 604, 608, 612 (e.g., a user computer, etc.) and can forward the web page requests and/or input data to the web (application) server 616. In further embodiments, the server 616 may function as a file server. Although for ease of description, FIG. 6 illustrates a separate web server 614 and file/application server 616, those skilled in the art will recognize that the functions described with respect to servers 614, 616 may be performed by a single server and/or a plurality of specialized servers, depending on implementation-specific needs and parameters. The computer systems 604, 608, 612, web (file) server 614 and/or web (application) server 616 may function as the system, devices, or components described in FIGS. 1-6.

The computing environment 600 may also include a database 618. The database 618 may reside in a variety of locations. By way of example, database 618 may reside on a storage medium local to (and/or resident in) one or more of the computers 604, 608, 612, 614, 616. Alternatively, it may be remote from any or all of the computers 604, 608, 612, 614, 616, and in communication (e.g., via the network 352) with one or more of these. The database 618 may reside in a storage-area network ("SAN") familiar to those skilled in the art. Similarly, any necessary files for performing the functions attributed to the computers 604, 608, 612, 614, 616 may be stored locally on the respective computer and/or remotely, as appropriate. The database 618 may be a relational database, such as Oracle 20i®, that is adapted to store, update, and retrieve data in response to SQL-formatted commands.

Figure 7:
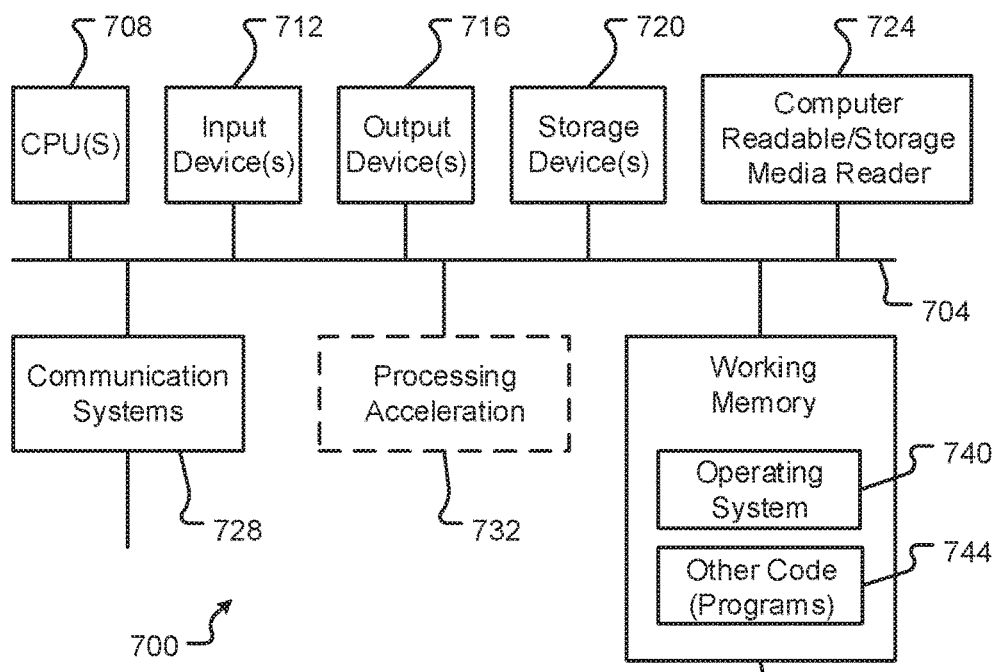
FIG. 7 is a block diagram of a computing device associated with one or more components described herein.

FIG. 7 illustrates one embodiment of a computer system 700 upon which the servers, user computers, computing devices, or other systems or components described above may be deployed or executed. The computer system 700 is shown comprising hardware elements that may be electrically coupled via a bus 704. The hardware elements may include one or more central processing units (CPUs) 708; one or more input devices 712 (e.g., a mouse, a keyboard, etc.); and one or more output devices 716 (e.g., a display device, a printer, etc.). The computer system 700 may also include one or more storage devices 720. By way of example, storage device(s) 720 may be disk drives, optical storage devices, solid-state storage devices such as a random access memory ("RAM") and/or a read-only memory ("ROM"), which can be programmable, flash-updateable and/or the like.

The computer system 700 may additionally include a computer-readable storage media reader 724; a communications system 728 (e.g., a modem, a network card (wireless or wired), an infra-red communication device, etc.); and working memory 736, which may include RAM and ROM devices as described above. The computer system 700 may also include a processing acceleration unit 732, which can include a DSP, a special-purpose processor, and/or the like.

The computer-readable storage media reader 724 can further be connected to a computer-readable storage medium, together (and, optionally, in combination with storage device(s) 720) comprehensively representing remote, local, fixed, and/or removable storage devices plus storage media for temporarily and/or more permanently containing computer-readable information. The communications system 728 may permit data to be exchanged with a network and/or any other computer described above with respect to the computer environments described herein. Moreover, as disclosed herein, the term "storage medium" may represent one or more devices for storing data, including read only memory (ROM), random access memory (RAM), magnetic RAM, core memory, magnetic disk storage mediums, optical storage mediums, flash memory devices and/or other machine readable mediums for storing information.

The computer system 700 may also comprise software elements, shown as being currently located within a working memory 736, including an operating system 740 and/or other code 744. It should be appreciated that alternate embodiments of a computer system 700 may have numerous variations from that described above. For example, customized hardware might also be used and/or particular elements might be implemented in hardware, software (including portable software, such as applets), or both. Further, connection to other computing devices such as network input/output devices may be employed.

Examples of the processors 340, 708 as described herein may include, but are not limited to, at least one of Qualcomm® Snapdragon® 800 and 801, Qualcomm® Snapdragon® 620 and 615 with 4G LTE Integration and 64-bit computing, Apple® A7 processor with 64-bit architecture, Apple® M7 motion coprocessors, Samsung® Exynos® series, the Intel® Core™ family of processors, the Intel® Xeon® family of processors, the Intel® Atom™ family of processors, the Intel Itanium® family of processors, Intel® Core® i5-4670K and i7-4770K 22 nm Haswell, Intel® Core® i5-3570K 22 nm Ivy Bridge, the AMD® FXT™ family of processors, AMD® FX-4300, FX-6300, and FX-8350 32 nm Vishera, AMD® Kaveri processors, Texas Instruments® Jacinto C6000™ automotive infotainment processors, Texas Instruments® OMAP™ automotive-grade mobile processors, ARM® Cortex™-M processors, ARM® Cortex-A and ARM926EJ-S™ processors, other industry-equivalent processors, and may perform computational functions using any known or future-developed standard, instruction set, libraries, and/or architecture.

Figure 8:
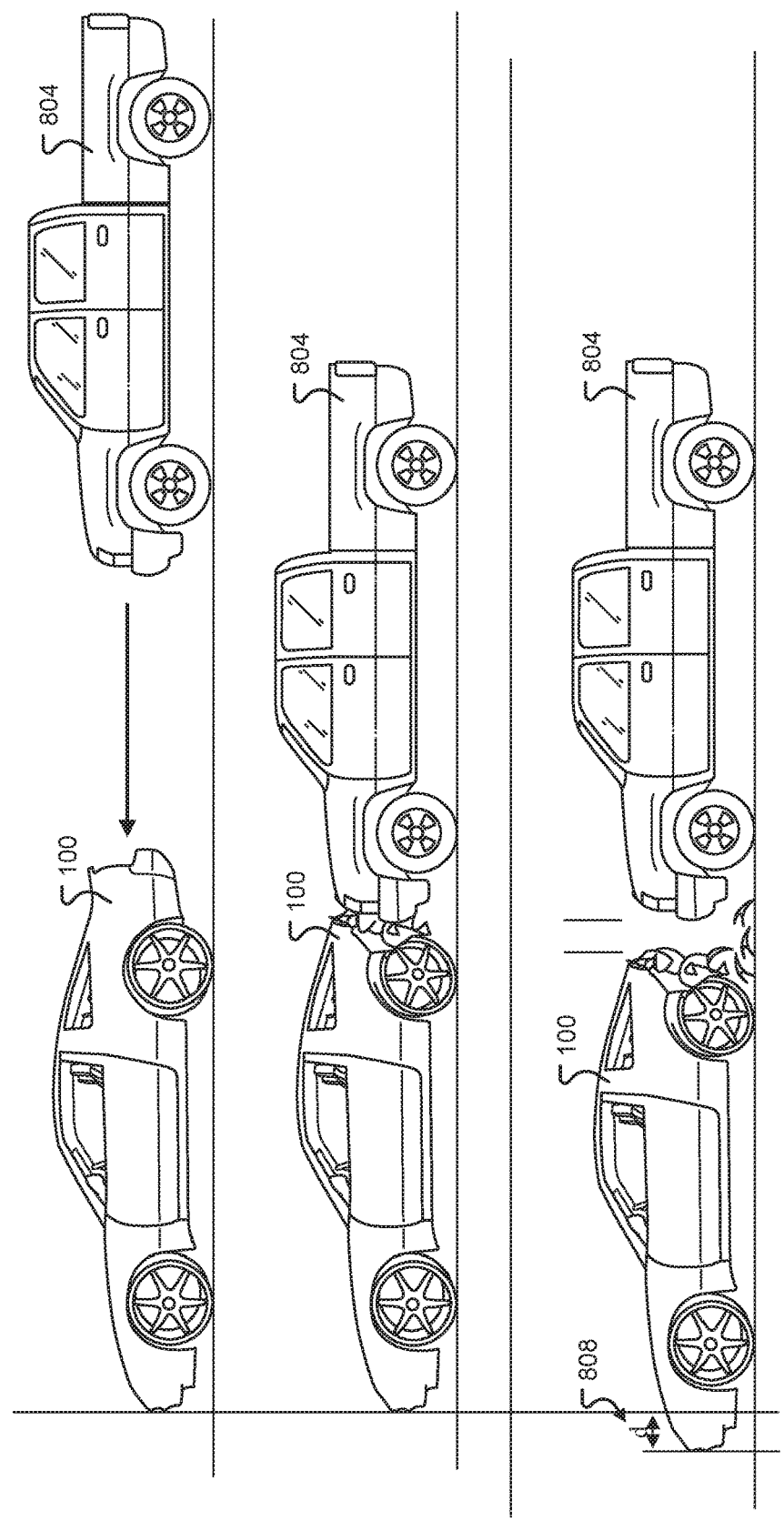
FIG. 8 is a first example of a collision.

FIG. 8 illustrates a first scenario in which a vehicle 804 collides with the vehicle 100. In some vehicles, such as those including a Mercedes-Benz PRE-SAFE® PLUS system, prior to an impending rear-end collision, the PRE-SAFE® PLUS system activates the rear hazard warning lights at a higher frequency than normal, thereby attracting the attention of the drivers of the vehicles following behind by flashing at an increased frequency. In the event of a sustained risk of collision, the PRE-SAFE® system implements protective measures for the occupants of the vehicle—including automatic belt tensioning. Further, if the vehicle 100 is stationary during the hazardous situation (e.g., impending collision), it is kept "firmly braked" immediately before the impact, thereby minimizing the forward jolt and reducing the risk of whiplash injuries for the occupants in some situations. As depicted in FIG. 8, however, because the vehicle 100 remains firmly braked, the vehicle 100 absorbs a significant amount of energy transferred from the vehicle 804 during the collision. Accordingly, vehicle 100 travels a minimal distance 808. In vehicles that can absorb such energy using crumple zones and other energy-absorbing techniques, such forward jolt may be minimized. That is, the purpose of crumple zones is to slow down the collision and to absorb energy to reduce the difference in speeds between the vehicle and its occupants. However, in other vehicles that may not be able to absorb such energy and/or in situations where road surfaces and/or tire surfaces make it difficult if not impossible to keep the vehicle firmly braked, there is an increased risk to the passengers within vehicle 100 due to initial shock (e.g., jolt) and forces attributable to the vehicle 100 absorbing and then dissipating a significant amount of energy in a short of amount of time when such vehicle moves a short distance.

Figure 9:
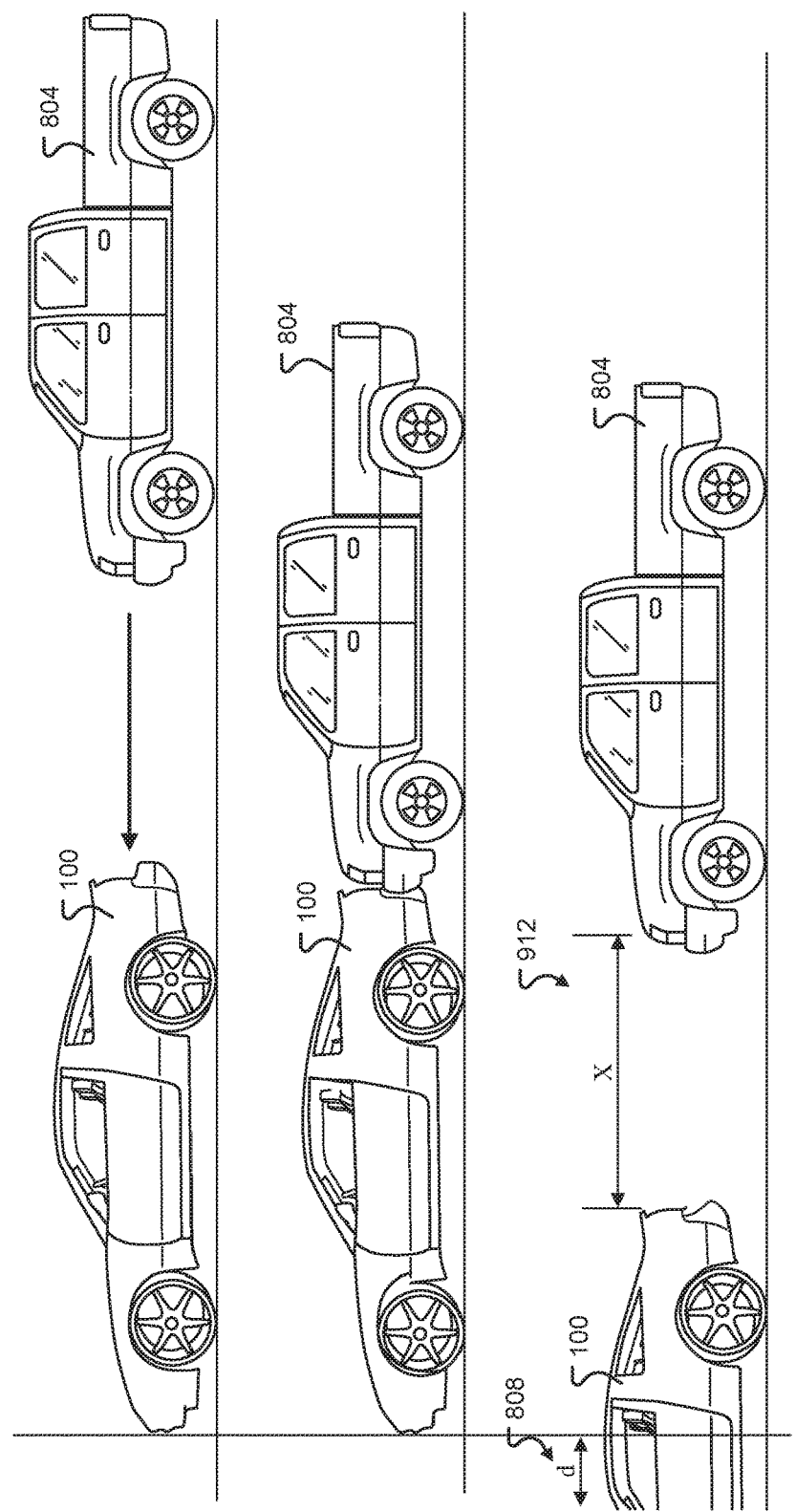
FIG. 9 is a first example of a collision in accordance with embodiments of the present disclosure.

Accordingly, embodiments of the present disclosure are directed to releasing the brake prior to and during a collision. As depicted in FIG. 9, while stopped, the vehicle 100 facing an impending collision from vehicle 804 may release the brakes such that during and after the collision, the vehicle 100 dissipates some of the energy transferred from the moving vehicle 804 over a distance 908, which is greater than a distance 808, and thereby a distance 912 between vehicles 100 and 804 increases. Thus, the braking of vehicle 100 can be applied over time such that a jolt (forward, backward, side, etc.) experienced by occupants of the vehicle 100 can be minimized. Of course, prior to releasing the brakes, the vehicle 100 may determine that by releasing the brakes, a greater risk of injury to the occupants and/or objects and/or persons around the vehicle 100 does not increase. Thus, the vehicle 100 may determine an escape path or route, if possible, and may further determine that it is likely safer to follow the escape path in the collision than attempt to stay stopped during the collision.

As depicted in FIG. 10A, an embodiment of a data structure 1000 representing sensor measurements associated with an object is depicted. The measurements 1004, 1008, 1012, 1016 represent one or more sensor measurements, such as those discussed above. Each measurement 1004-1016 can be associated with a time 1020, 1024, 1028, 1032. The time is from a present moment to some time in the past. As such, the measurements 1004-1016 represent a series of measurements of an object over a time period that is separated into portions 1020, 1024, 1028, and 1032.

Each time portion 1020, 1024, 1028, 1032 may be at a predetermined interval, e.g., 5 microseconds, 20 milliseconds, etc. A most recent measurement 1032 may be made at time 0. Each preceding measurement 1004, 1008, 1012 may be made at time 0 minus some number of time portions (e.g., 10 time portions before, 5 time portions before, etc.). For example, time measurement 1008 may be time 0 minus Y, where Y represent 19 time portions (19 times 5 microseconds or 95 microseconds) in the past.

There can be any number of time portions 1020, 1024, 1028, 1032 that result in any number of measurements 1004, 1008, 1012, 1016, as represented by ellipses 1026. As such, the number of stored measurements 1004, 1008, 1012, 1016 can be predetermined or may be set by a user based on the accuracy of the measurement results desired. Further, the time portions 1020, 1024, 1028, 1032 can also be predetermined or user established also based on the accuracy of the measurement desired or the speed at which the sensors or processor can functionally obtain or analyze the measurements.

Each object around the vehicle 100 can have a set of measurements while the object is within physical proximity of the vehicle (e.g., 100 yards, 100 feet, etc.) based on whether the location of the object may affect an escape path of the vehicle 100 and/or whether such object represents a potential and/or impending collision. Thus, while the vehicle 100 is stopped, objects in back of the vehicle 100 or behind the general direction of travel of the vehicle 100 may be measured more often or measured more accurately than those objects in front of the vehicle 100. As any number of objects may be within physical proximity of the vehicle 100, there may be more than a single data structure 1000 stored by the vehicle processor 708, as represented by ellipses 1036.

An embodiment of another data structure 1038 representing constraints on how the vehicle 100 may maneuver or on how an object may behave may be as shown in FIG. 10B. In a first configuration, the constraints 1040, 1044, 1048, 1052 can represent one or more constraints on a vehicle 100. A constraint can be characteristics of the driving ability of the vehicle 100. For example, a constraint 1040, 1044, 1048, 1052 can include one or more of, but is not limited to, a steering range, an acceleration limit, an acceleration limit at a specific speed, a braking limit, a gravity force rating for the tires, a skid limit, etc.

Any of the constraints can be added to or modified by the context of the situation in which the vehicle 100 is driving or stopped. For example, if the vehicle 100 is driving in snow or rain, the friction between the tires and the detected road surface and/or road surface condition together with the steering limits may change. Moreover, a direction in which an impending collision is sensed may alter one or more constraints 1040, 1044, 1048, 1052. For example, the steering ability or maneuverability may be different depending on a sensed direction of an impending collision. These constraints 1040, 1044, 1048, 1052, thus, can be learned or modified over time based on machine learning or based on database updates that result from the experience of this vehicle 100 or similar vehicles, as provided by a manufacturer.

In an alternative or additional embodiment, the constraints 1040, 1044, 1048, 1052 can represent one or more constraints on an object. Thus, the constraints 1040, 1044, 1048, 1052 can be characteristics associated with the behavior of other objects around the vehicle 100. For example, a constraint 1040, 1044, 1048, 1052 can include one or more of, but is not limited to: a likely steering ability of another vehicle, an acceleration limit for another vehicle, an acceleration limit at a specific speed for another vehicle, a braking limit for another vehicle, a gravity-force rating for the tires for another vehicle, a skid limit for another vehicle, a speed of a pedestrian, a speed of a bicycle, a behavior trait for another vehicle, a driving situation (based on street signs, traffic signals, lane markers, road barriers, construction zones, etc.), a rule, a law, a sensed or perceived value or worth, and other constraints. For example, a perceived value or worth for an object such as a road barrier may be less than a perceived value or worth of a pedestrian.

Any of the constraints can be added to or modified by the context of the situation in which the vehicle 100 is driving. Again, for example, if the vehicle 100 is driving in snow or rain, the deceleration and steering limits can change. The steering ability or maneuverability may be different for vehicles around the vehicle 100. These object constraints 1040, 1044, 1048, 1052, thus, can be learned or modified over time based on machine learning that result from the experience of this vehicle 100 or another vehicle, as provided by a manufacturer.

There can be any number of the constraints 1040, 1044, 1048, 1052, as represented by ellipses 1056. As such, the number of stored constraints 1040, 1044, 1048, 1052 can be predetermined or may be set by a user based on how accurately the object or vehicle 100 behavior is to be determined. Each object encountered by the vehicle 100 can have a set of constraints. Thus, there may be more data structures 1038 than those shown in FIG. 10B, as represented by ellipses 1060.

In order to determine whether or not to release the brakes prior to and/or during an impending collision, the likely path of another vehicle or object and/or the location of another vehicle or object around the vehicle 100 needs to be determined. To accomplish the determination of the path of the object and/or the path of the vehicle 100, the processor 708 can, for example, apply stochastic modeling to determine the probabilistic path and/or location of an object in order to determine an escape route, if any, for the vehicle 100. The stochastic process is a probability model used to describe phenomena that evolves over time and/or space. For another vehicle or object, a stochastic process is a time sequence representing the evolution of movement of the vehicle or object represented by a position in three-dimensional (or two-dimensional) space, where the position change is subject to a random variation. The output of the stochastic model is a probability that the vehicle or object will be in a particular position at some time "t" in the future. In using the stochastic process, the movement of the vehicle or object to the next state or position depends, at least partially, on the current state and or past states, as measured by the sensors and described in conjunction with FIG. 10A. Further, the stochastic process measuring the further position of the vehicle or object can also be based, at least partially, on the constraints 1038, described in conjunction with FIG. 10B.

Figure 11:
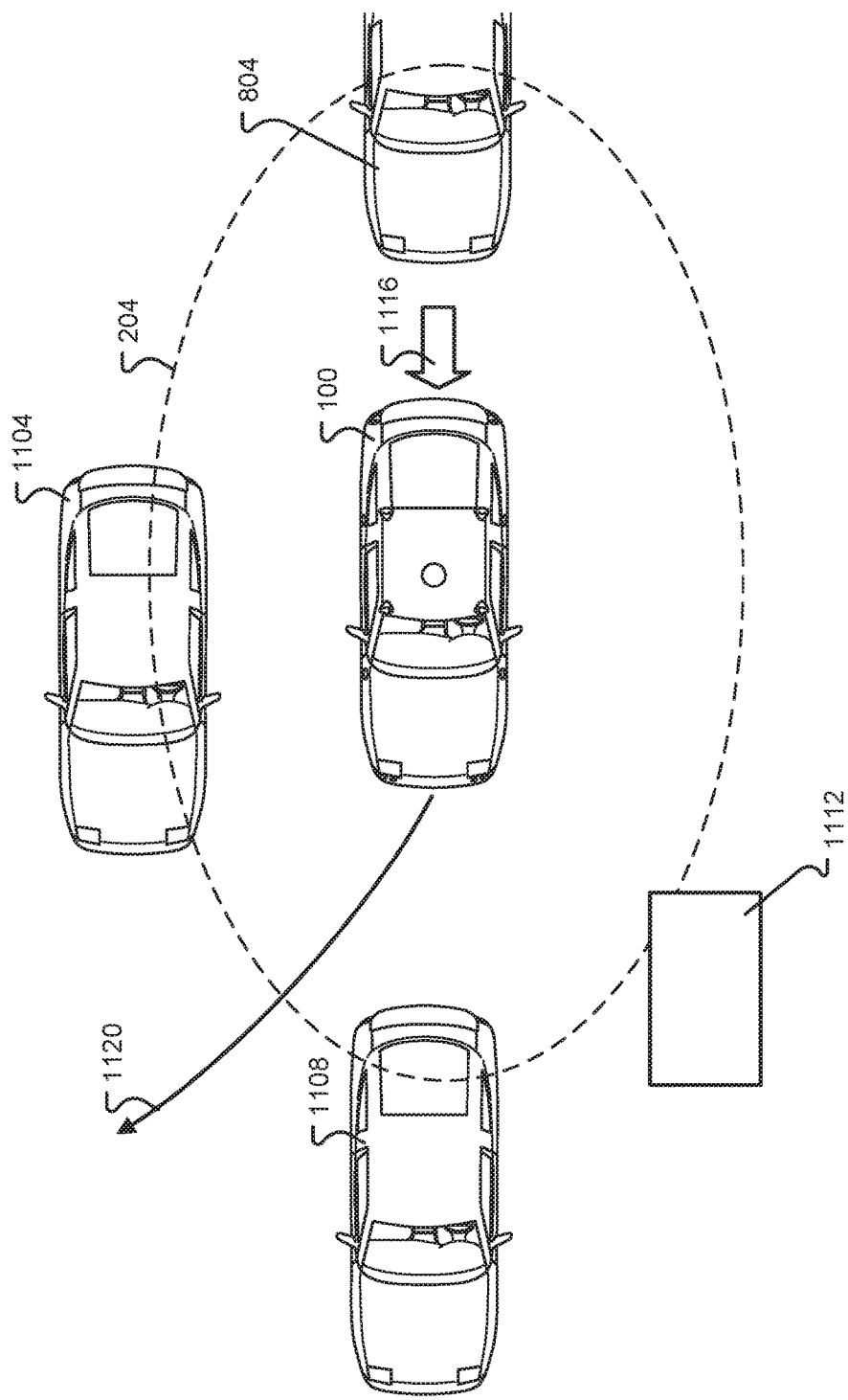
FIG. 11 illustrates a first example of disengaging a brake function and/or determining an escape path in accordance with embodiments of the present disclosure.

In accordance with embodiments of the present disclosure, FIG. 11 illustrates a first example of determining whether to release brakes on vehicle 100 prior to and/or during a collision and is based on detected objects around the vehicle 100 and a determined escape path. As depicted in FIG. 11, an imminent collision transferring an amount of energy 1116 for example, may be detected by one or more sensors 116K, 116J, and/or sensing zone 216K within the effective detection limit 204. That is, in addition to detecting that a collision may be imminent, the processor(s) 708 may determine an amount of kinetic energy 1116 and/or momentum and/or a probability of an amount of energy and/or momentum being transferred to vehicle 100 during a collision. Accordingly, in some instances, when the amount of energy and/or momentum is low for example, the brakes may not need to be released to dissipate such transferred energy and/or momentum. In other instances, when the amount of transferred energy and/or momentum 1116 is high, the brakes may be released to assist in absorbing and/or redirecting some energy. The amount of energy and/or momentum 1116 may be associated with an object, or vehicle, as one characteristic for example and as previously described.

As depicted in FIG. 11, objects 1104, 1108, and/or 1112 may be near vehicle 100 and may be detected by one or more sensors as previously described. The processor 708 may determine and/or assign one or more characteristics as previously described to the objects 1104, 1108, and/or 1112. In instances where, like the vehicle 100, the objects 1104, 1108, and/or 1112 are stationary, determining an escape route or path 1120 may be fairly straightforward such that the vehicle control system 348 releases the brakes and steers the vehicle 100 between objects 1104 and 1108 along the escape route 1120. Of course, the determination as to whether the brakes can be released is based on whether an escape route 1120 can be calculated and at least the amount of energy and/or momentum 1116 that may be transferred—such determination may be determined and/or estimated based on a variety of characteristics of the vehicle 100 and vehicle 804. Examples of characteristics include, but are not limited to, a velocity of a vehicle 804 about to collide with the vehicle 100, an estimated mass of the vehicle 804, a deceleration associated with the vehicle 804, an estimated angle of impact between the vehicle 804 and the vehicle 100, a type of pavement, a condition of the pavement, a weather condition, and/or a reaction time of the driver. Of course, more or less characteristics may be considered.

As previously discussed, a stochastic model may be utilized to determine an escape route. The stochastic model may utilize the characteristics as previously discussed and determine a path, over time, which would allow the brakes to be applied in a gentler way such that the vehicle 100 comes to a stop and an amount of shock and/or force exerted on the occupants within the vehicle 100 is minimized. That is, although the brakes may be released during a collision, following the collision the brakes are applied in a gentler manner. The objects 1104 and 1108 may be vehicles as depicted in FIG. 11, while object 1112 may be, but is not limited to, one or more pedestrians, bicyclist, crowded market, stationary object, ditch, canyon, intersection, oncoming traffic lane, and/or area that would be dangerous to individuals in the area or within the vehicle 100. Accordingly, an escape route 1120 may be determined and, upon the sensed and imminent collision, the vehicle control system 348 may cause the brakes to be released and may automatically steer the vehicle 100 along the determined escape route 1120. In some embodiments, the amount of control, such as the degree of braking release and/or the degree of steering may be influenced by the vehicle's level of automation.

Figure 12:
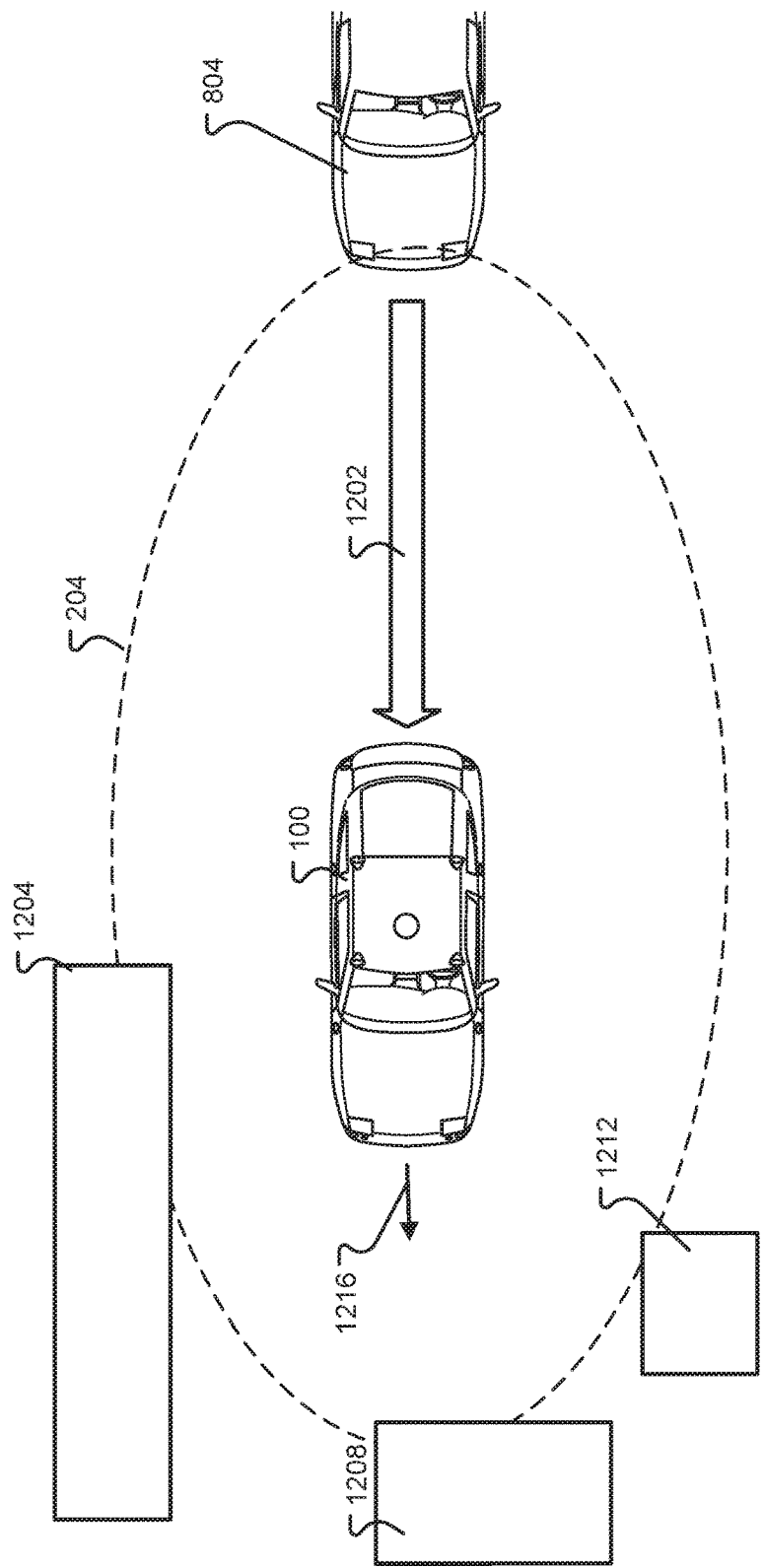
FIG. 12 illustrates a second example of disengaging a brake function and/or determining an escape path in accordance with embodiments of the present disclosure.

In accordance with embodiments of the present disclosure, FIG. 12 depicts another example of determining an escape route. The escape route 1216 may not involve any steering and may include a momentary release of the brakes such that the vehicle 100 can dissipate energy and/or momentum 1202 transferred from the collision with vehicle 804. Alternatively, or in addition, the processor(s) 708 may not be able to determine an escape route. Accordingly, the processor(s) 708 may determine that the safest course of action is to keep the brakes locked to keep the occupants and those individuals around the vehicle 100 most safe. Moreover, in that the processor 708 may determine a plurality of escape routes, the processor(s) 708 may determine a safety factor and/or probability associated with each escape route. Accordingly, the escape route 1216 may be one of many determined escape routes.

Figure 10C:
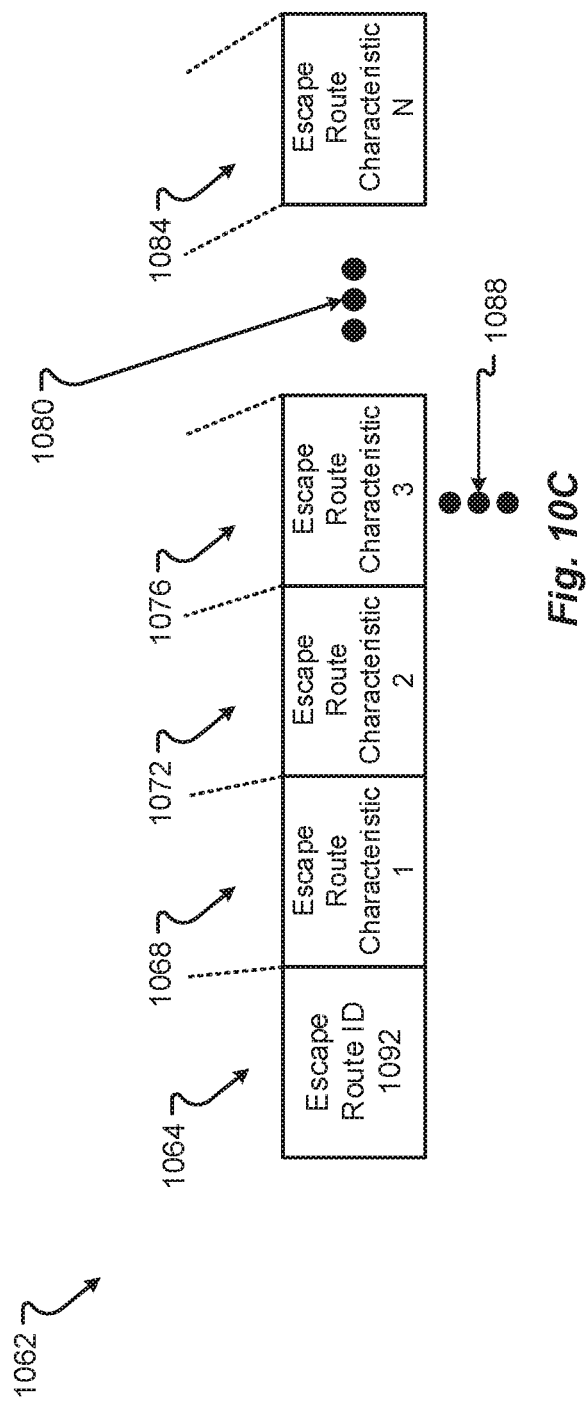

An embodiment of another data structure 1062 representing characteristics of one or more escape routes for a vehicle 100 is shown in FIG. 10C. In a first configuration, the characteristics 1068, 1072, 1076, 1080, and 1084 can represent one or more characteristics of one or more escape routes. For example, a characteristic 1068, 1072, 1076, 1080, and 1084 may include, but is not limited to, one or more of a probability of an escape route being followed, a quantifiable amount of injury attributable to the escape route, a monetary amount attributable to the injuries resulting from the escape route, and/or an amount of predicted damage (for example, a monetary amount) associated with the escape route.

Any of the characteristics can be added to or modified by the context of the situation in which the vehicle 100 is driving or stopped. Furthermore, an identity of one or more occupants of the vehicle 100 and/or pedestrians, or other occupants of other vehicles may determine one or more characteristics 1068, 1072, 1076, 1080, and 1084. For example, knowing that a pedestrian or other driver is recovering from a previous injury may affect a monetary amount associated with injuries of the escape route. Thus, these characteristics 1068, 1072, 1076, 1080, and 1084 can be learned or modified over time based on machine learning or based on database updates that result from the experience of this vehicle 100 or similar vehicles, as provided by a manufacturer. There can be any number of the characteristics 1068, 1072, 1076, 1080, and 1084 as represented by ellipses 1080 and any number escape paths as indicated by ellipses 1088. Moreover, each escape path may have a unique ID 1064. As most collisions occur for a short duration of time, each of the escape routes may have a time-to-live characteristic which indicates how long each escape route may be selectable.

Figure 13:
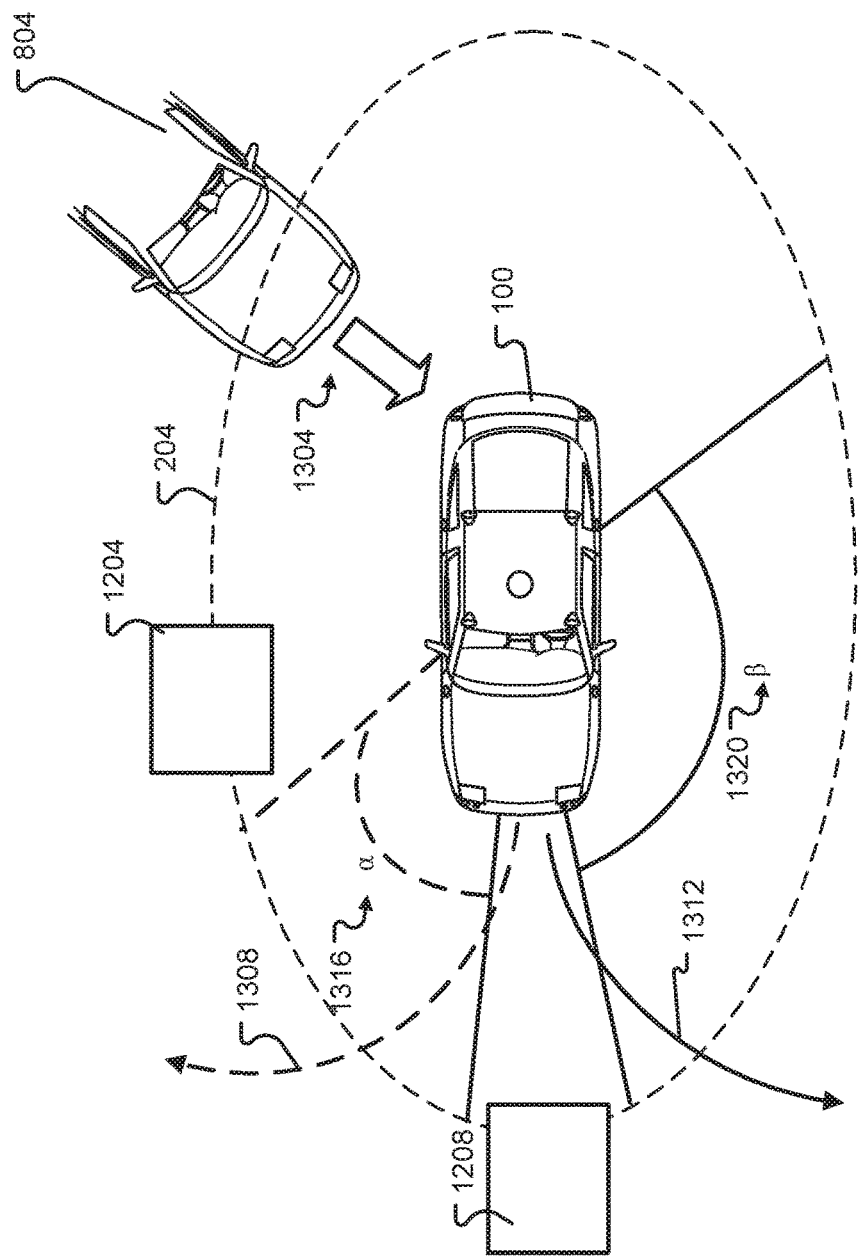
FIG. 13 illustrates a third example of disengaging a brake function and/or determining an escape path in accordance with embodiments of the present disclosure.

In accordance with embodiments of the present disclosure, FIG. 13 depicts another example of releasing the brakes of a vehicle 100 and calculating an escape route when an angle of collision between the vehicle 100 and the vehicle 804 is not directly from behind as previously illustrated. In such an instance, one or more escape routes may be determined based on an amount of energy and/or momentum transferred to the vehicle 100 from the vehicle 804 causing the vehicle 100 to spin and/or move in a direction other than a direction in which the tires roll and/or a direction of travel. Accordingly, the vehicle control system 348 may take into account such angle, an amount of friction between the tires and road surface based on a direction of movement of the tires, and energy and/or momentum dissipation as previously mentioned. As depicted in FIG. 13, objects 1204 and 1208 may be around the vehicle 100 and may be detected by one or more of the previously described sensors; during a rear end collision, the escape routes 1308 and 1312 may be determined and may correspond to escape angles of 1316 and 1320. That is, an escape angle may be a range of angles 1316 and 1320 in which the vehicle control system 348 may steer the vehicle 100 to avoid objects 1204 and 1208. However, because the energy and/or momentum 1304 may be imparted on the vehicle 100 at an angle, the angles 1316 and routes 1308 may not be safe. Accordingly, the stochastic model may drop such angles and routes from a list of one or more safe angles and/or routes. Thus, the vehicle control system 348 may cause the brakes to be released and steer the vehicle in a direction of one or more angles 1316 and/or routes 1308. As previously discussed, such routes may reside and may be maintained in the data structure 1062; accordingly, the routes may be updated, deleted, and/or modified in some manner.

Figure 14:
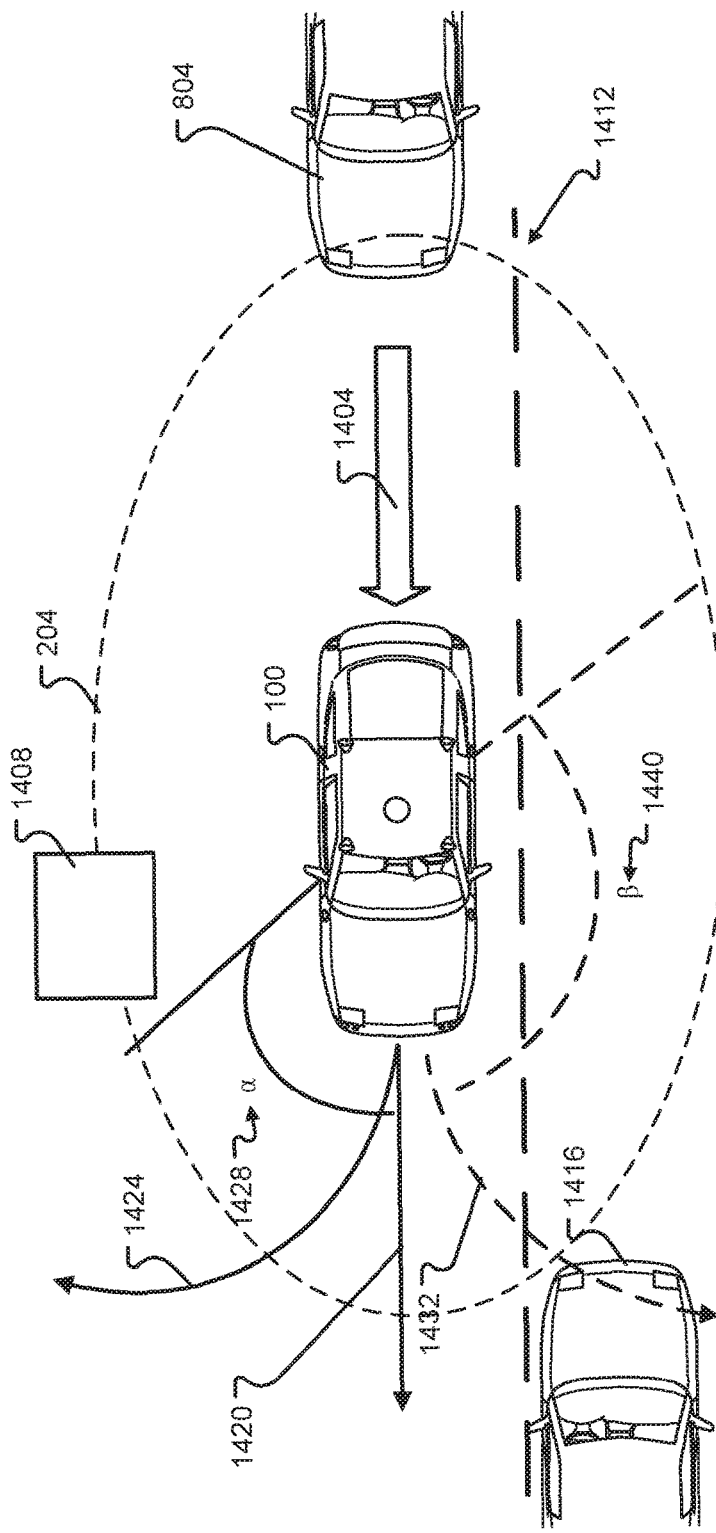
FIG. 14 illustrates a fourth example of disengaging a brake function and/or determining an escape path in accordance with embodiments of the present disclosure.

FIG. 14 depicts another example of releasing vehicle 100 brakes based on calculated escape routes in accordance with embodiments of the present disclosure. Vehicle 100 may be stopped, or otherwise stationary, and may be adjacent to an oncoming traffic lane 1412. As the vehicle 804 approaches the vehicle 100, one or more sensors as previously discussed may be utilized to determine that a collision is imminent. Accordingly, the processor 708 may determine a plurality of escape routes to avoid object 1408. The energy and/or momentum 1404 may cause vehicle 100 to move in a direction 1420; however, the processor 708 may determine escape routes 1424, 1420, and/or 1432 in addition to escape angles 1428 and/or 1440 in which vehicle 100 may travel with brakes released. In that vehicle 100 may be steered along escape path 1432 because vehicle 1416 has yet to be detected by one or more sensors and/or sensor zones as previously described, the processor 708 may alter one or more escape route characteristics such that crossing a center lane into a traffic lane 1412 negatively impacts the escape route 1432 selection. That is, because an escape route, namely escape route 1420 is viable, such escape route 1420 is determined to be a safer option because it does not require vehicle 100 to cross into a traffic lane with potentially oncoming traffic. Thus, escape route 1432 and escape angle 1440 may be removed from the data structure 1062.

Figure 15:
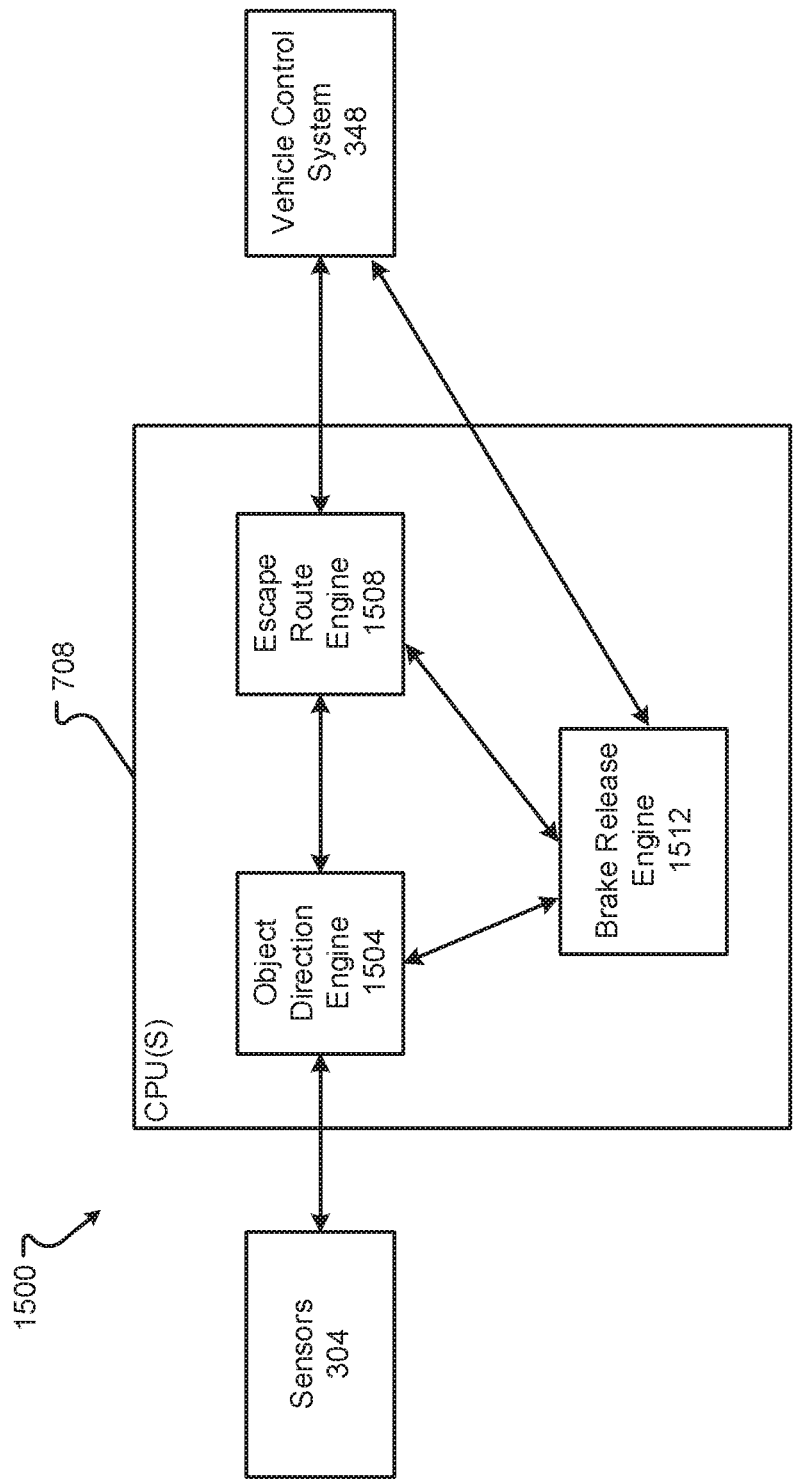
FIG. 15 is a block diagram of a computing system associated with one or more components described herein.

An embodiment of a software and/or hardware system that may be executed as part of the CPU 708 or may be embodied in an application specific integrated circuit (ASIC), a system-on-chip (SoC), field programmable gate array (FPGA), or other type of hardware device may be as shown in FIG. 15. The system 1500 can include one or more different components that can be in communication with the vehicle control system 348 as described previously. As such, the vehicle control system 348 can receive the information from the different components 1504, 1508, 1512 to control the vehicle 100 to release the braking mechanisms and steer the vehicle 100 along a safe escape route. The different components can include one or more of, but are not limited to: an object direction/detection engine 1504, an escape route engine 1508, and/or a brake release engine 1512.

The object direction/detection engine 1504 can be the processing component that creates and outputs results from the stochastic model as explained previously. Thus, the object direction/detection engine 1504 can receive data from the one or more sensors 304 and provide a determination as to where each of the objects may reside and/or are predicted to reside, as explained previously in conjunction with FIGS. 8 through 14. This object information and the algorithms used therein may produce an output that is provided to the escape route engine 1508.

The escape route engine 1508 can process the analysis of object locations and/or predicted locations to determine both the probability of a collision in any one position at any time "T" in the future and provides the best escape path, for the vehicle 100, without having a collision with another object. The escape route engine 1508 can receive both the object information 1504 and the information in the constraints 1038 to determine which path the vehicle 100 can or may move to best avoid any possible additional collisions. This information may be stored in the data structure 1062 and/or provided to the vehicle control system 348 to use in controlling the vehicle 100 to maneuver along the best path.

In accordance with embodiments of the present disclosure, the information provided from the escape route engine 1508 may be provided to the brake release engine 1512; thus, when a valid escape route has been determined, the brake release engine 1512 may determine, further based on environmental characteristics if needed, that the brakes can be released prior to and/or during a collision. The brake release engine may provide information to the vehicle control system 348 such that the brakes can be released.

Figure 16:
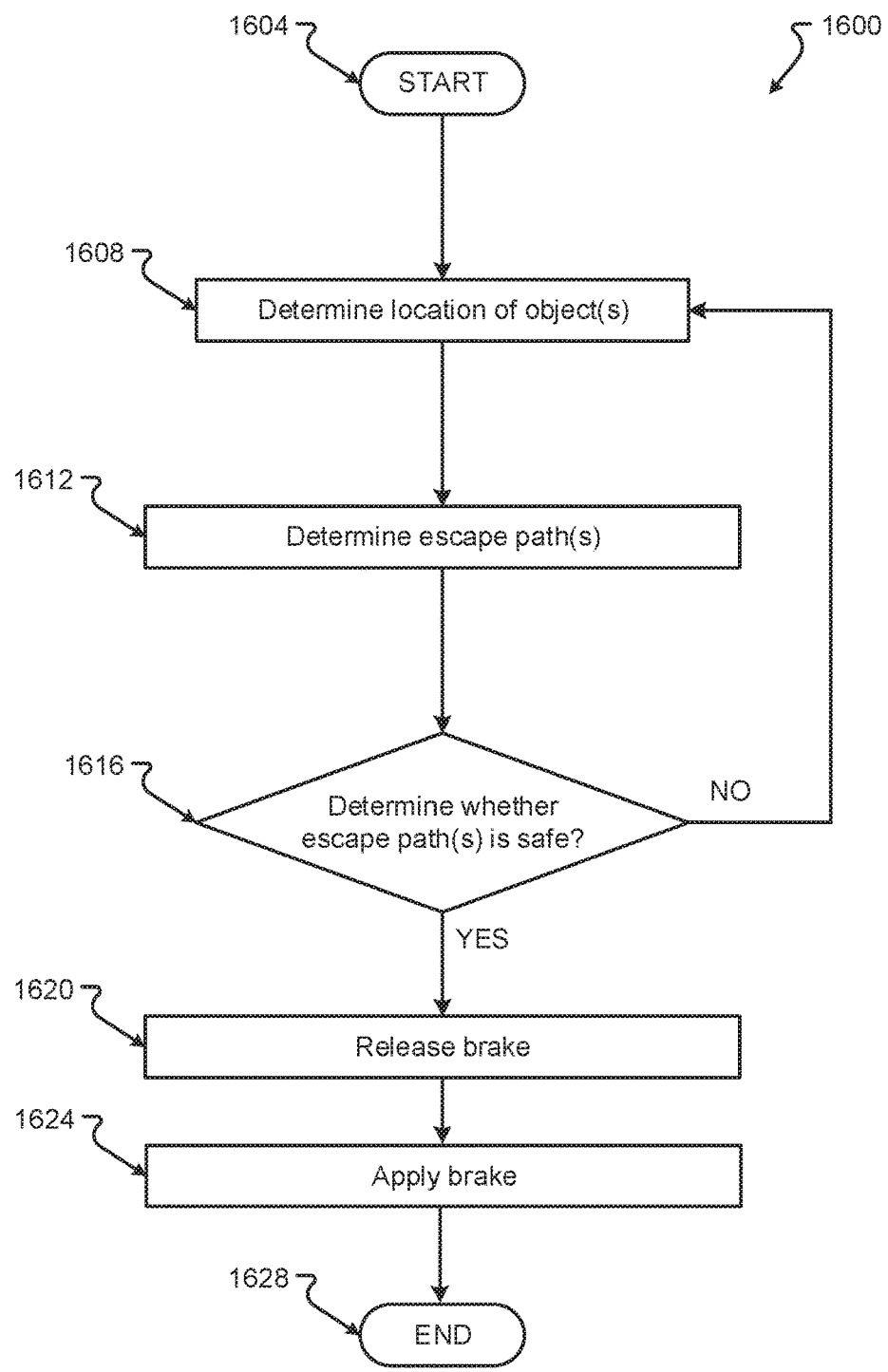
FIG. 16 is a first flow diagram of an embodiment of a method for disengaging a braking function and/or steering a vehicle along an escape path in accordance with embodiments of the present disclosure.

An embodiment of a method 1600 for determining when to release the brakes may be shown in FIG. 16 in accordance with embodiments of the present disclosure. A general order for the steps of the method 1600 is shown in FIG. 16. Generally, the method 1600 starts with a start operation 1604 and ends with an end operation 1628. The method 1600 can include more or fewer steps or can arrange the order of the steps differently than those shown in FIG. 16. The method 1600 can be executed as a set of computer-executable instructions executed by a computer system or processor and encoded or stored on a computer readable medium. In other configurations, the method 1600 may be executed by a series of components, circuits, gates, etc. created in a hardware device, such as a System of Chip (SOC), Application Specific Integrated Circuit (ASIC), and/or a Field Programmable Gate Array (FPGA). Hereinafter, the method 1600 shall be explained with reference to the systems, components, circuits, modules, software, data structures, signaling processes, models, environments, vehicles, etc. described in conjunction with FIGS. 1-15.

In step 1608, the object direction/detection engine 1504 can determine the trajectory and/or location of one or more objects surrounding the vehicle 100 in the vehicle's environment and/or within the effective detection limit 204. For example, as shown in FIG. 14, the effective detection limit 204 around the vehicle may include the current vehicle 100 and one or more objects, for example, vehicle 804, and object 1408. The vehicle 100 can receive sensor data 304 over some period of time that may help to determine the location, actual and predicted, for each of the vehicles 804 and/or object 1408 as previously described. Such information about the vehicle 804 and/or the object 1408 may be added to the data structure 1000.

At step 1612, one or more escape paths may be determined by the escape route engine 1508. As depicted in FIG. 14, multiple escape routes 1420, 1424, and 1432 may be determined, and as previously discussed, such escape routes may be stored in the date structure 1062. At step 1616, one or more escape routes may be chosen based on a safety factor. If such an escape route is selected, the brake release engine 1512 may determine, based on a multitude of factors and as previously described, whether the brakes should be released. If the brake release engine 1512 determines that the brakes should be released (or not engaged), the vehicle control system 348 may cause the brakes to be released and the vehicle 100 may be steered along the chosen and/or selected escape path at step 1620. If it is determined that none of the escape paths are safe, the method 1600 may return to step 1608 where the method 1600 repeats. Once determined that the vehicle 100 may be slowed without causing jolt and/or other harm to the occupants within the vehicle 100, the vehicle control system 348 may cause the brakes to engage slowly and in a more gentle way and reduce the speed of the vehicle 100 at step 1624. The method may end at step 1628.

Figure 17:
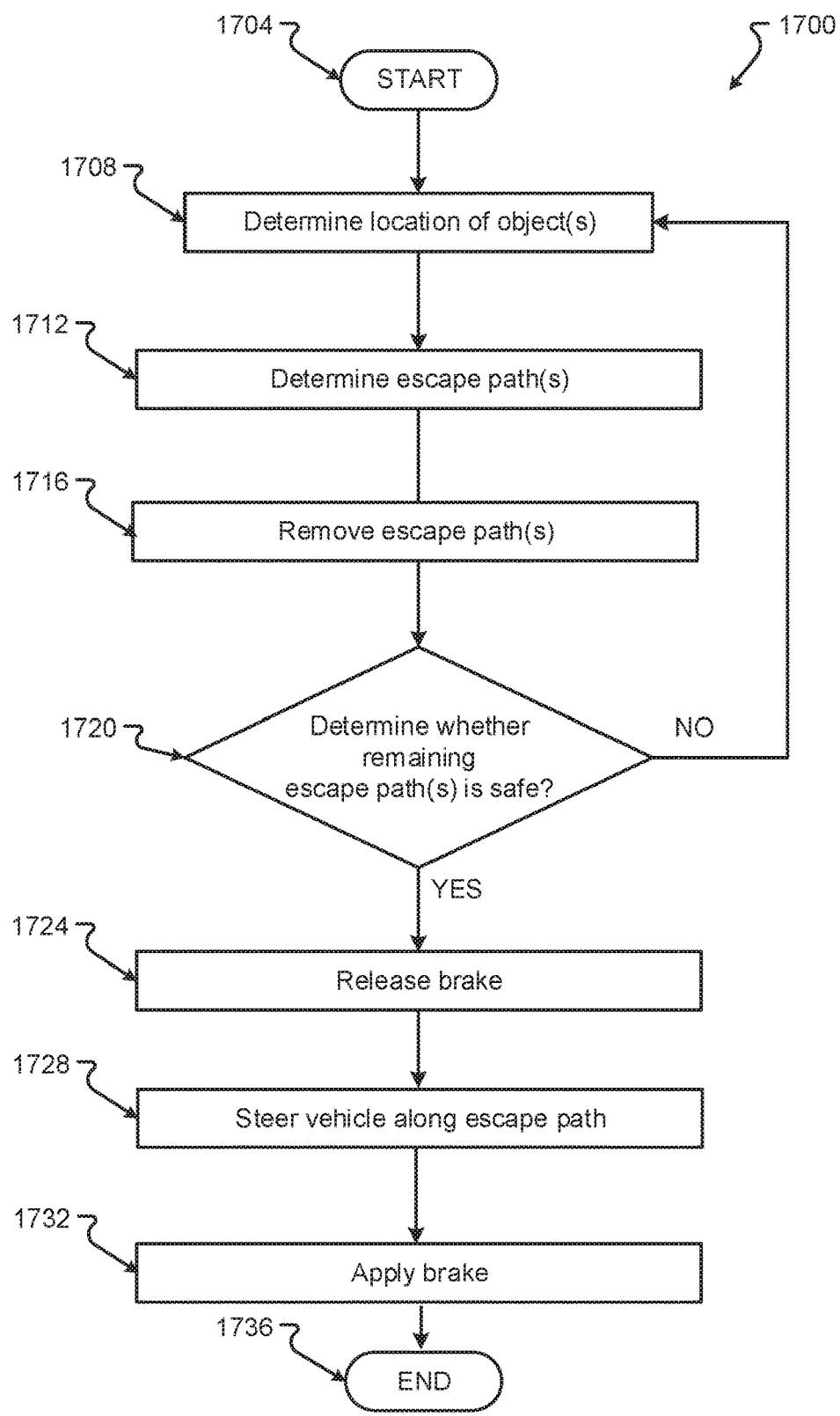
FIG. 17 is a second flow diagram of an embodiment of a method for disengaging a braking function and/or steering a vehicle along an escape path in accordance with embodiments of the present disclosure.

An embodiment of a method 1700 for determining when to release the brakes may be shown in FIG. 17 in accordance with embodiments of the present disclosure. A general order for the steps of the method 1700 is shown in FIG. 17. Generally, the method 1700 starts with a start operation 1704 and ends with an end operation 1736. The method 1700 can include more or fewer steps or can arrange the order of the steps differently than those shown in FIG. 17. The method 1700 can be executed as a set of computer-executable instructions executed by a computer system or processor and encoded or stored on a computer-readable medium. In other configurations, the method 1700 may be executed by a series of components, circuits, gates, etc. created in a hardware device, such as a System of Chip (SOC), Application Specific Integrated Circuit (ASIC), and/or a Field Programmable Gate Array (FPGA). Hereinafter, the method 1700 shall be explained with reference to the systems, components, circuits, modules, software, data structures, signaling processes, models, environments, vehicles, etc. described in conjunction with FIGS. 1-16.

In step 1708, the object direction/detection engine 1504 can determine the trajectory and/or location of one or more objects surrounding the vehicle 100 in the vehicle's environment and/or within the effective detection limit 204. For example, as shown in FIG. 14, the effective detection limit 204 around the vehicle may include the current vehicle 100 and one or more objects, for example, vehicle 804, and object 1408. The vehicle 100 can receive sensor data 304 over some period of time that may help to determine the location, actual and predicted, for each of the vehicles 804 and/or object 1408 as previously described. Such information about the vehicle 804 and/or the object 1408 may be added to the data structure 1000.

At step 1712, one or more escape paths may be determined by the escape route engine 1508. As depicted in FIG. 14, multiple escape routes 1420, 1424, and 1432 may be determined, and as previously discussed, such escape routes may be stored in the date structure 1062. At step 1716, one or more escape paths may be removed from a data structure, such as data structure 1062. In instances where escape paths may be viable, but a safer escape path is available or such collision from vehicle 804 makes implementing the escape path difficult, the one or more escape paths may be removed. At step 1720, one or more escape routes may be chosen based on a safety factor. If such an escape route is selected, the brake release engine 1512 may determine, based on a multitude of factors and as previously described, whether the brakes should be released. If the brake release engine 1512 determines that the brakes should be released (or not engaged), the vehicle control system 348 may cause the brakes to be released at step 1724 and the vehicle may be steered at step 1728 along the chosen and/or selected escape path. If it is determined that none of the escape paths are safe, the method 1700 may return to step 1708 where the method 1700 repeats. Once determined that the vehicle 100 may be slowed without causing jolt and/or other harm to the occupants within the vehicle 100, the vehicle control system may cause the brakes to engage slowly and in a more gentle way and reduce the speed of the vehicle 100 at step 1732. The method may end at step 1736.

Figure 18:
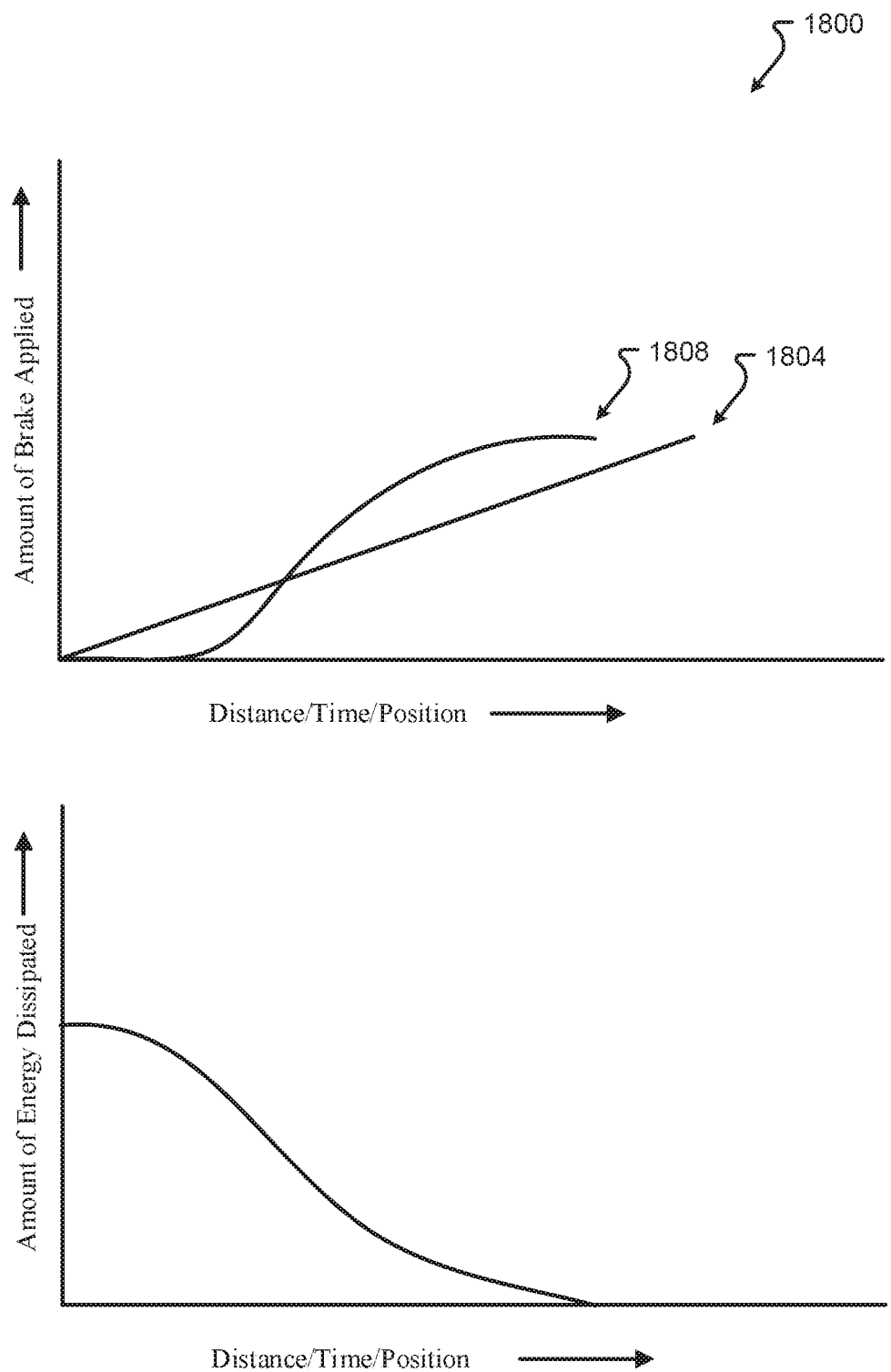
FIG. 18 is an example of a braking operation in accordance with embodiments of the present disclosure.

FIG. 18 depicts an example 1800 of an amount of braking applied to slow the vehicle 100. As depicted in FIG. 18, an amount of braking may be applied to reduce an amount of energy and/or momentum of the vehicle 100 such that vehicle 100 slows and stops. That is, one or more braking profiles may be enacted; such profiles may be non-linear such as 1804 and/or linear such as 1808. As further depicted in FIG. 18, as a braking operation is performed, an amount of energy and/or momentum of the vehicle 100 decreases.

Any of the steps, functions, and operations discussed herein can be performed continuously and automatically.

The exemplary systems and methods of this disclosure have been described in relation to vehicle systems and electric vehicles. However, to avoid unnecessarily obscuring the present disclosure, the preceding description omits a number of known structures and devices. This omission is not to be construed as a limitation of the scope of the claimed disclosure. Specific details are set forth to provide an understanding of the present disclosure. It should, however, be appreciated that the present disclosure may be practiced in a variety of ways beyond the specific detail set forth herein.

Furthermore, while the exemplary embodiments illustrated herein show the various components of the system collocated, certain components of the system can be located remotely, at distant portions of a distributed network, such as a LAN and/or the Internet, or within a dedicated system. Thus, it should be appreciated, that the components of the system can be combined into one or more devices, such as a server, communication device, or collocated on a particular node of a distributed network, such as an analog and/or digital telecommunications network, a packet-switched network, or a circuit-switched network. It will be appreciated from the preceding description, and for reasons of computational efficiency, that the components of the system can be arranged at any location within a distributed network of components without affecting the operation of the system.

Furthermore, it should be appreciated that the various links connecting the elements can be wired or wireless links, or any combination thereof, or any other known or later developed element(s) that is capable of supplying and/or communicating data to and from the connected elements. These wired or wireless links can also be secure links and may be capable of communicating encrypted information. Transmission media used as links, for example, can be any suitable carrier for electrical signals, including coaxial cables, copper wire, and fiber optics, and may take the form of acoustic or light waves, such as those generated during radio-wave and infra-red data communications.

While the flowcharts have been discussed and illustrated in relation to a particular sequence of events, it should be appreciated that changes, additions, and omissions to this sequence can occur without materially affecting the operation of the disclosed embodiments, configuration, and aspects.

A number of variations and modifications of the disclosure can be used. It would be possible to provide for some features of the disclosure without providing others.

In yet another embodiment, the systems and methods of this disclosure can be implemented in conjunction with a special purpose computer, a programmed microprocessor or microcontroller and peripheral integrated circuit element(s), an ASIC or other integrated circuit, a digital signal processor, a hard-wired electronic or logic circuit such as discrete element circuit, a programmable logic device or gate array such as PLD, PLA, FPGA, PAL, special purpose computer, any comparable means, or the like. In general, any device(s) or means capable of implementing the methodology illustrated herein can be used to implement the various aspects of this disclosure. Exemplary hardware that can be used for the present disclosure includes computers, handheld devices, telephones (e.g., cellular, Internet enabled, digital, analog, hybrids, and others), and other hardware known in the art. Some of these devices include processors (e.g., a single or multiple microprocessors), memory, nonvolatile storage, input devices, and output devices. Furthermore, alternative software implementations including, but not limited to, distributed processing or component/object distributed processing, parallel processing, or virtual machine processing can also be constructed to implement the methods described herein.

In yet another embodiment, the disclosed methods may be readily implemented in conjunction with software using object or object-oriented software development environments that provide portable source code that can be used on a variety of computer or workstation platforms. Alternatively, the disclosed system may be implemented partially or fully in hardware using standard logic circuits or VLSI design. Whether software or hardware is used to implement the systems in accordance with this disclosure is dependent on the speed and/or efficiency requirements of the system, the particular function, and the particular software or hardware systems or microprocessor or microcomputer systems being utilized.

In yet another embodiment, the disclosed methods may be partially implemented in software that can be stored on a storage medium, executed on programmed general-purpose computer with the cooperation of a controller and memory, a special purpose computer, a microprocessor, or the like. In these instances, the systems and methods of this disclosure can be implemented as a program embedded on a personal computer such as an applet, JAVA® or CGI script, as a resource residing on a server or computer workstation, as a routine embedded in a dedicated measurement system, system component, or the like. The system can also be implemented by physically incorporating the system and/or method into a software and/or hardware system.

Although the present disclosure describes components and functions implemented in the embodiments with reference to particular standards and protocols, the disclosure is not limited to such standards and protocols. Other similar standards and protocols not mentioned herein are in existence and are considered to be included in the present disclosure. Moreover, the standards and protocols mentioned herein and other similar standards and protocols not mentioned herein are periodically superseded by faster or more effective equivalents having essentially the same functions. Such replacement standards and protocols having the same functions are considered equivalents included in the present disclosure.

The present disclosure, in various embodiments, configurations, and aspects, includes components, methods, processes, systems and/or apparatus substantially as depicted and described herein, including various embodiments, subcombinations, and subsets thereof. Those of skill in the art will understand how to make and use the systems and methods disclosed herein after understanding the present disclosure. The present disclosure, in various embodiments, configurations, and aspects, includes providing devices and processes in the absence of items not depicted and/or described herein or in various embodiments, configurations, or aspects hereof, including in the absence of such items as may have been used in previous devices or processes, e.g., for improving performance, achieving ease, and/or reducing cost of implementation.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments, configurations, or aspects for the purpose of streamlining the disclosure. The features of the embodiments, configurations, or aspects of the disclosure may be combined in alternate embodiments, configurations, or aspects other than those discussed above. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment, configuration, or aspect. Thus, the following claims are hereby incorporated into this Detailed Description, with each claim standing on its own as a separate preferred embodiment of the disclosure.

Moreover, though the description of the disclosure has included description of one or more embodiments, configurations, or aspects and certain variations and modifications, other variations, combinations, and modifications are within the scope of the disclosure, e.g., as may be within the skill and knowledge of those in the art, after understanding the present disclosure. It is intended to obtain rights, which include alternative embodiments, configurations, or aspects to the extent permitted, including alternate, interchangeable and/or equivalent structures, functions, ranges, or steps to those claimed, whether or not such alternate, interchangeable and/or equivalent structures, functions, ranges, or steps are disclosed herein, and without intending to publicly dedicate any patentable subject matter.

Embodiments include a vehicle, comprising one or more sensors sensing an environment surrounding the vehicle, a vehicle control system autonomously controlling a braking function of the vehicle, a processor in communication with the sensor and the vehicle control system, the processor configured to identify an object within the environment, determine an escape path to avoid the object, and disengage the braking function.

Aspects of the above vehicle include where the vehicle control system autonomously controls a steering function of the vehicle, and the processor is configured to steer the vehicle along the escape path. Aspects of the above vehicle include where the vehicle is stationary prior to the braking function being disengaged. Aspects of the above vehicle include where the processor is configured to determine that a collision is imminent. Aspects of the above vehicle include where the collision is between the vehicle and another vehicle. Aspects of the above vehicle include where the processor is configured to engage the braking function to reduce a velocity of the vehicle after the braking function has been disengaged. Aspects of the above vehicle include where the processor is configured to reduce the velocity of the vehicle at a predetermined rate. Aspects of the above vehicle include where the processor is configured to estimate a mass, a velocity, and a trajectory of another vehicle, and further communicate with the another vehicle to at least one of avoid a collision or mitigate a collision impact on vehicle occupant.

Embodiments include a method that includes sensing an environment surrounding a vehicle by one or more sensors, sending sensor information to a processor, identifying, by the processor, an object within the environment, determining, by the processor, an escape path to avoid the object, and disengaging a braking function.

Aspects of the above method include autonomously controlling a steering function of the vehicle, and steering the vehicle along the escape path. Aspects of the above method include where the vehicle is stationary prior to the braking function being disengaged. Aspects of the above method include determining that a collision is imminent. Aspects of the above method include where the collision is between the vehicle and another vehicle. Aspects of the above method include engaging the braking function to reduce a velocity of the vehicle after the braking function has been disengaged. Aspects of the above method include reducing the velocity of the vehicle at a predetermined rate.

Embodiments include a non-transitory information storage media having stored thereon one or more instructions, that when executed by one or more processors, cause a processor to perform a method, the method including sensing an environment surrounding a vehicle by one or more sensors, sending sensor information to a processor, identifying, by the processor, an object within the environment, determining, by the processor, an escape path to avoid the object, and disengaging a braking function.

Aspects of the above non-transitory information storage media include autonomously controlling a steering function of the vehicle, and steering the vehicle along the escape path. Aspects of the above non-transitory information storage media include where the vehicle is stationary prior to the braking function being disengaged. Aspects of the above non-transitory information storage media include determining that a collision is imminent, wherein the collision is between the vehicle and another vehicle. Aspects of the above non-transitory information storage media include engaging the braking function to reduce a velocity of the vehicle after the braking function has been disengaged.

Any one or more of the aspects/embodiments as substantially disclosed herein.

Any one or more of the aspects/embodiments as substantially disclosed herein optionally in combination with any one or more other aspects/embodiments as substantially disclosed herein.

One or means adapted to perform any one or more of the above aspects/embodiments as substantially disclosed herein.

The phrases "at least one," "one or more," "or," and "and/or" are open-ended expressions that are both conjunctive and disjunctive in operation. For example, each of the expressions "at least one of A, B and C," "at least one of A, B, or C," "one or more of A, B, and C," "one or more of A, B, or C," "A, B, and/or C," and "A, B, or C" means A alone, B alone, C alone, A and B together, A and C together, B and C together, or A, B and C together.

The term "a" or "an" entity refers to one or more of that entity. As such, the terms "a" (or "an"), "one or more," and "at least one" can be used interchangeably herein. It is also to be noted that the terms "comprising," "including," and "having" can be used interchangeably.

The term "automatic" and variations thereof, as used herein, refers to any process or operation, which is typically continuous or semi-continuous, done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material."

Aspects of the present disclosure may take the form of an embodiment that is entirely hardware, an embodiment that is entirely software (including firmware, resident software, micro-code, etc.) or an embodiment combining software and hardware aspects that may all generally be referred to herein as a "circuit," "module," or "system." Any combination of one or more computer-readable medium(s) may be utilized. The computer-readable medium may be a computer-readable signal medium or a computer-readable storage medium.

A computer-readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer-readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer-readable storage medium may be any tangible medium that can contain or store a program for use by or in connection with an instruction execution system, apparatus, or device.

A computer-readable signal medium may include a propagated data signal with computer-readable program code embodied therein, for example, in baseband or as part of a carrier wave. Such a propagated signal may take any of a variety of forms, including, but not limited to, electromagnetic, optical, or any suitable combination thereof. A computer-readable signal medium may be any computer-readable medium that is not a computer-readable storage medium and that can communicate, propagate, or transport a program for use by or in connection with an instruction execution system, apparatus, or device. Program code embodied on a computer-readable medium may be transmitted using any appropriate medium, including, but not limited to, wireless, wireline, optical fiber cable, RF, etc., or any suitable combination of the foregoing.

The terms "determine," "calculate," "compute," and variations thereof, as used herein, are used interchangeably and include any type of methodology, process, mathematical operation or technique.

The term "electric vehicle" (EV), also referred to herein as an electric drive vehicle, may use one or more electric motors or traction motors for propulsion. An electric vehicle may be powered through a collector system by electricity from off-vehicle sources, or may be self-contained with a battery or generator to convert fuel to electricity. An electric vehicle generally includes a rechargeable electricity storage system (RESS) (also called Full Electric Vehicles (FEV)). Power storage methods may include: chemical energy stored on the vehicle in on-board batteries (e.g., battery electric vehicle or BEV), on board kinetic energy storage (e.g., flywheels), and/or static energy (e.g., by on-board double-layer capacitors). Batteries, electric double-layer capacitors, and flywheel energy storage may be forms of rechargeable on-board electrical storage.

The term "hybrid electric vehicle" refers to a vehicle that may combine a conventional (usually fossil fuel-powered) powertrain with some form of electric propulsion. Most hybrid electric vehicles combine a conventional internal combustion engine (ICE) propulsion system with an electric propulsion system (hybrid vehicle drivetrain). In parallel hybrids, the ICE and the electric motor are both connected to the mechanical transmission and can simultaneously transmit power to drive the wheels, usually through a conventional transmission. In series hybrids, only the electric motor drives the drivetrain, and a smaller ICE works as a generator to power the electric motor or to recharge the batteries. Power-split hybrids combine series and parallel characteristics. A full hybrid, sometimes also called a strong hybrid, is a vehicle that can run on just the engine, just the batteries, or a combination of both. A mid hybrid is a vehicle that cannot be driven solely on its electric motor, because the electric motor does not have enough power to propel the vehicle on its own.

The term "rechargeable electric vehicle" or "REV" refers to a vehicle with on board rechargeable energy storage, including electric vehicles and hybrid electric vehicles.

What is claimed is:

1. A vehicle, comprising:
   one or more sensors sensing an environment surrounding the vehicle;
   a vehicle control system autonomously controlling a braking function of the vehicle;
   a processor in communication with the one or more sensors and the vehicle control system, the processor programmed to:
   identify an object within the environment via information received from the one or more sensors;
   determine, based on the information received from the one or more sensors, that the object is about to collide with the vehicle;
   determine a location of other objects in proximity to the vehicle;
   determine, prior to a collision with the object and based on the location of the other objects in proximity to the vehicle, an escape path and escape angle for the vehicle to follow upon colliding with the object;

determine, based on the information received from the one or more sensors, to control the braking function of the vehicle to reduce a force of impact when colliding with the object;

disengage the braking function of the vehicle prior to and during a collision with the object; and control autonomously a steering function of the vehicle to steer the vehicle at the escape angle and along the escape path around the other objects in proximity to the vehicle.

2. The vehicle of claim 1, wherein the processor is configured to steer the vehicle along the escape path during and after the collision using energy and momentum transferred to the vehicle from the collision with the object.

3. The vehicle of claim 2, wherein the vehicle is stationary prior to the braking function being disengaged.

4. The vehicle of claim 3, wherein the processor is configured to determine, based on information associated with the object approaching the vehicle, that the collision between the object and the vehicle is imminent.

5. The vehicle of claim 4, wherein prior to determining the escape path and escape angle for the vehicle to follow upon colliding with the object, the processor is further configured to:

determine that a risk of injury to an occupant of the vehicle does not increase by disengaging the braking function of the vehicle.

6. The vehicle of claim 2, wherein the processor is configured to engage the braking function to reduce a velocity of the vehicle and the object after the collision and after the braking function has been disengaged.

7. The vehicle of claim 6, wherein the processor is configured to reduce the velocity of the vehicle at a predetermined rate.

8. The vehicle of claim 2, wherein the processor is configured to estimate a mass, a velocity, and a trajectory of another vehicle, and further communicate with the another vehicle to mitigate a force associated with the collision experienced by an occupant of the vehicle.

9. A method, comprising:

sensing an environment surrounding a vehicle by one or more sensors;

sending sensor information to a processor;

identifying, by the processor and based on the sensor information received from the one or more sensors, an object within the environment;

determining, by the processor and based on the information received from the one or more sensors, that the object is about to collide with the vehicle;

determining, by the processor, a location of other objects in proximity to the vehicle;

determining, by the processor prior to a collision with the object and based on the location of the other objects in proximity to the vehicle, an escape path and an escape angle for the vehicle to follow upon colliding with the object;

determining, by the processor and based on the information received from the one or more sensors, to autonomously control a braking function of the vehicle to reduce a force of impact when colliding with the object;

disengaging the braking function of the vehicle prior to and during a collision with the object; and controlling, autonomously by the processor, a steering function of the vehicle to steer the vehicle at the escape angle and along the escape path around the other objects in proximity to the vehicle.

10. The method of claim 9, further comprising:

steering the vehicle along the escape path during and after the collision using energy and momentum transferred to the vehicle from the collision with the object.

11. The method of claim 10, wherein the vehicle is stationary prior to the braking function being disengaged.

12. The method of claim 11, further comprising:

determining, via the processor and based on information associated with the object approaching the vehicle, that the collision between the object and the vehicle is imminent.

13. The method of claim 12, wherein prior to determining the escape path and escape angle for the vehicle to follow upon colliding with the object, the method further comprises:

determining that a risk of injury to an occupant of the vehicle does not increase by disengaging the braking function of the vehicle.

14. The method of claim 10, further comprising:

engaging the braking function to reduce a velocity of the vehicle and the object after the collision and after the braking function has been disengaged.

15. The method of claim 14, further comprising:

reducing the velocity of the vehicle at a predetermined rate.

16. A non-transitory information storage media having stored thereon one or more instructions, that when executed by a processor, cause the processor to perform a method, the method comprising:

sensing an environment surrounding a vehicle by one or more sensors;

sending sensor information to the processor;

identifying, by the processor and based on the sensor information received from the one or more sensors, an object within the environment;

determining, by the processor and based on the information received from the one or more sensors, that the object is about to collide with the vehicle;

determining, by the processor, a location of other objects in proximity to the vehicle;

determining, by the processor prior to a collision with the object and based on the location of the other objects in proximity to the vehicle, an escape path and an escape angle for the vehicle to follow upon colliding with the object;

determining, by the processor and based on the information received from the one or more sensors, to autonomously control a braking function of the vehicle to reduce a force of impact when colliding with the object;

disengaging the braking function of the vehicle prior to and during a collision with the object; and controlling, autonomously by the processor, a steering function of the vehicle to steer the vehicle at the escape angle and along the escape path around the other objects in proximity to the vehicle.

17. The non-transitory information storage media of claim 16, further comprising:

steering the vehicle along the escape path during and after the collision using energy and momentum transferred to the vehicle from the collision with the object.

18. The non-transitory information storage media of claim 17, wherein the vehicle is stationary prior to the braking function being disengaged.

19. The non-transitory information storage media of claim 18, further comprising:

determining, via the processor and based on information associated with the object approaching the vehicle, that the collision is imminent, wherein the collision is between the vehicle and another vehicle.

20. The non-transitory information storage media of claim 17, further comprising:
engaging the braking function to reduce a velocity of the vehicle and the object after the collision and after the braking function has been disengaged.

* * * * *